(12) United States Patent
McCash et al.

(10) Patent No.: US 8,030,088 B2
(45) Date of Patent: Oct. 4, 2011

(54) SAMPLE COLLECTION APPARATUS

(75) Inventors: Elaine Marie McCash, Comberton (GB); Nicol John Murray, Luton (GB)

(73) Assignee: Rapid Biosensor Systems Limited, Cambridge (GB)

( * ) Notice: Subject to any disclaimer, the term of this patent is extended or adjusted under 35 U.S.C. 154(b) by 884 days.

(21) Appl. No.: 11/999,690

(22) Filed: Dec. 6, 2007

(65) Prior Publication Data

US 2010/0279271 A1    Nov. 4, 2010

Related U.S. Application Data

(63) Continuation-in-part of application No. 10/474,877, filed on Apr. 5, 2004, now Pat. No. 7,384,793.

(30) Foreign Application Priority Data

| Apr. 11, 2001 | (GB) | .................................... 0108993.7 |
| Aug. 31, 2001 | (GB) | .................................... 0121039.2 |
| Sep. 24, 2001 | (GB) | .................................... 0122881.6 |
| Oct. 30, 2001 | (GB) | .................................... 0126001.7 |
| Jan. 8, 2002  | (GB) | .................................... 0200265.7 |

(51) Int. Cl.
*G01N 22/00* (2006.01)

(52) U.S. Cl. .................. 436/164; 435/283.1; 435/286.3; 435/288.7; 436/172; 427/2.11; 427/10

(58) Field of Classification Search ........................ None
See application file for complete search history.

(56) References Cited

U.S. PATENT DOCUMENTS

| 3,871,375 | A |   | 3/1975  | Bennett |
| 5,082,629 | A |   | 1/1992  | Burgess et al. |
| 5,348,885 | A | * | 9/1994  | Labarthe ..................... 435/305.4 |
| 5,747,333 | A | * | 5/1998  | Jungmann-Campello et al. ........................ 435/283.1 |
| 5,866,430 | A |   | 2/1999  | Grow |
| 5,904,900 | A |   | 5/1999  | Bleuse et al. |
| 6,828,110 | B2|   | 12/2004 | Lee et al. |
| 7,384,793 | B2| * | 6/2008  | McCash et al. ............... 436/172 |

(Continued)

FOREIGN PATENT DOCUMENTS

WO    9405567    5/1994

(Continued)

OTHER PUBLICATIONS

"Sensitivity Enhancement of Evanescent Wave Immunoassay"—Measurement Science and Technology, IOP Publishing, Bristol, GB, vol. 4, No. 10, Oct. 1, 1993, pp. 1077-1079, Masakazu Yoshida et al.

(Continued)

*Primary Examiner* — N. C. Yang
(74) *Attorney, Agent, or Firm* — Galgano & Associates, PLLC; Thomas M. Galgano; Jessica G. Bower

(57) ABSTRACT

A sample collection apparatus which measures biological samples and can be used to provide the early detection of respiratory diseases, for example tuberculosis induced by the pathogen *mycobacterium tuberculosis*. The sample collection apparatus has a sample collection unit and a corresponding complementary reader unit. The collection unit collects a sample exhaled from the user through a collection vessel with an optical interrogation region. The sample is spread on the inside of the vessel over the interrogation region and subsequently analyzed. The test results are displayed via the reader unit.

10 Claims, 22 Drawing Sheets

U.S. PATENT DOCUMENTS

2002/0106771 A1* 8/2002 Ullrich et al. .................. 435/194
2003/0068814 A1* 4/2003 Malinge ..................... 435/309.1
2003/0114379 A1* 6/2003 Li et al. ........................... 514/12

FOREIGN PATENT DOCUMENTS

| WO | 9614860 | 8/1996 |
|---|---|---|
| WO | 0121634 | 7/2001 |

OTHER PUBLICATIONS

"Detection of Antibody-Antigen Reactions at a Glass Liquid Interface as a Novel Optical Immunoassay Concept"—Proceedings of Second Optical Fibre conference (Stuttgart 1984) PP75 R.M. Sutherland et al.

\* cited by examiner

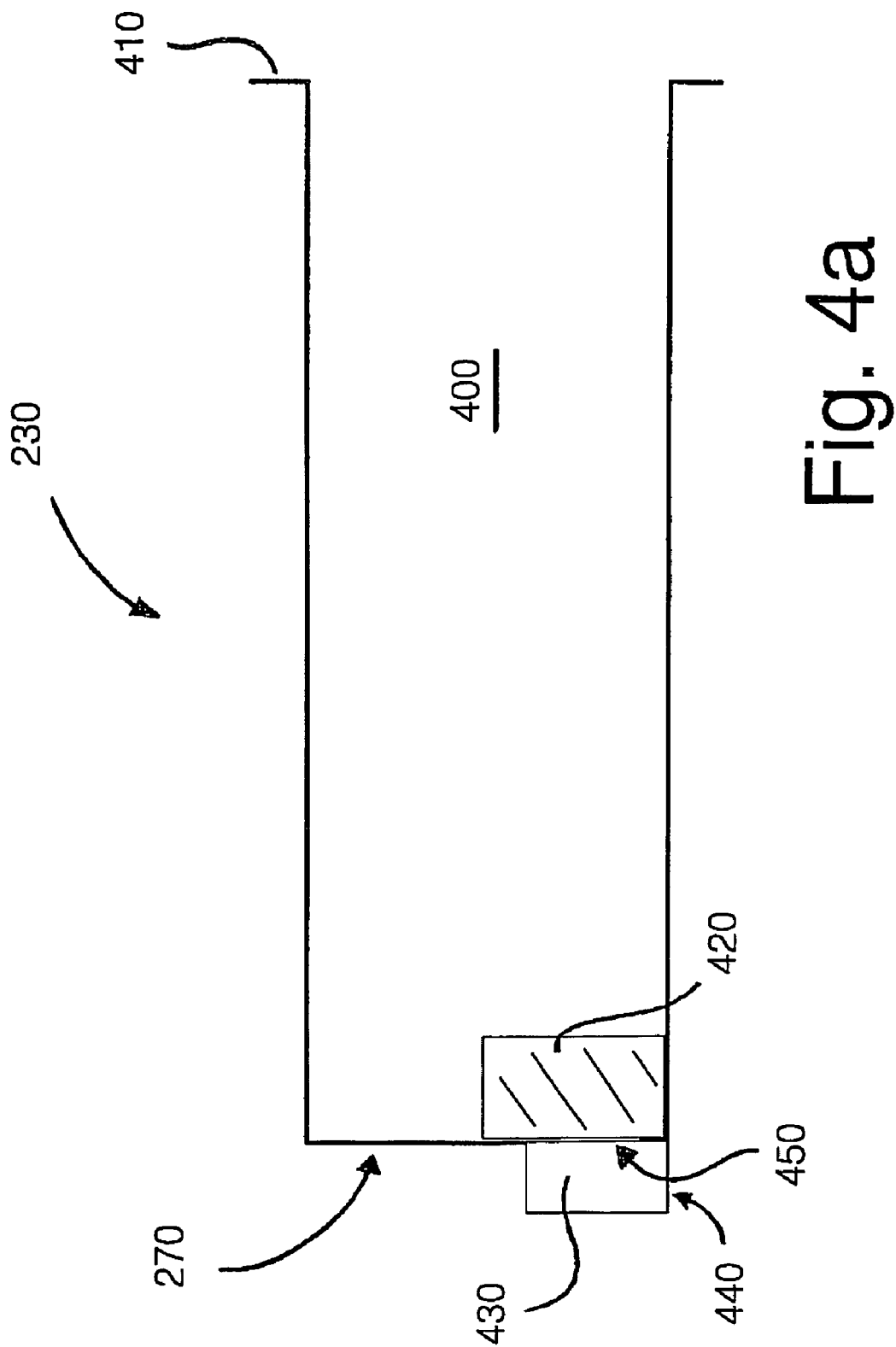

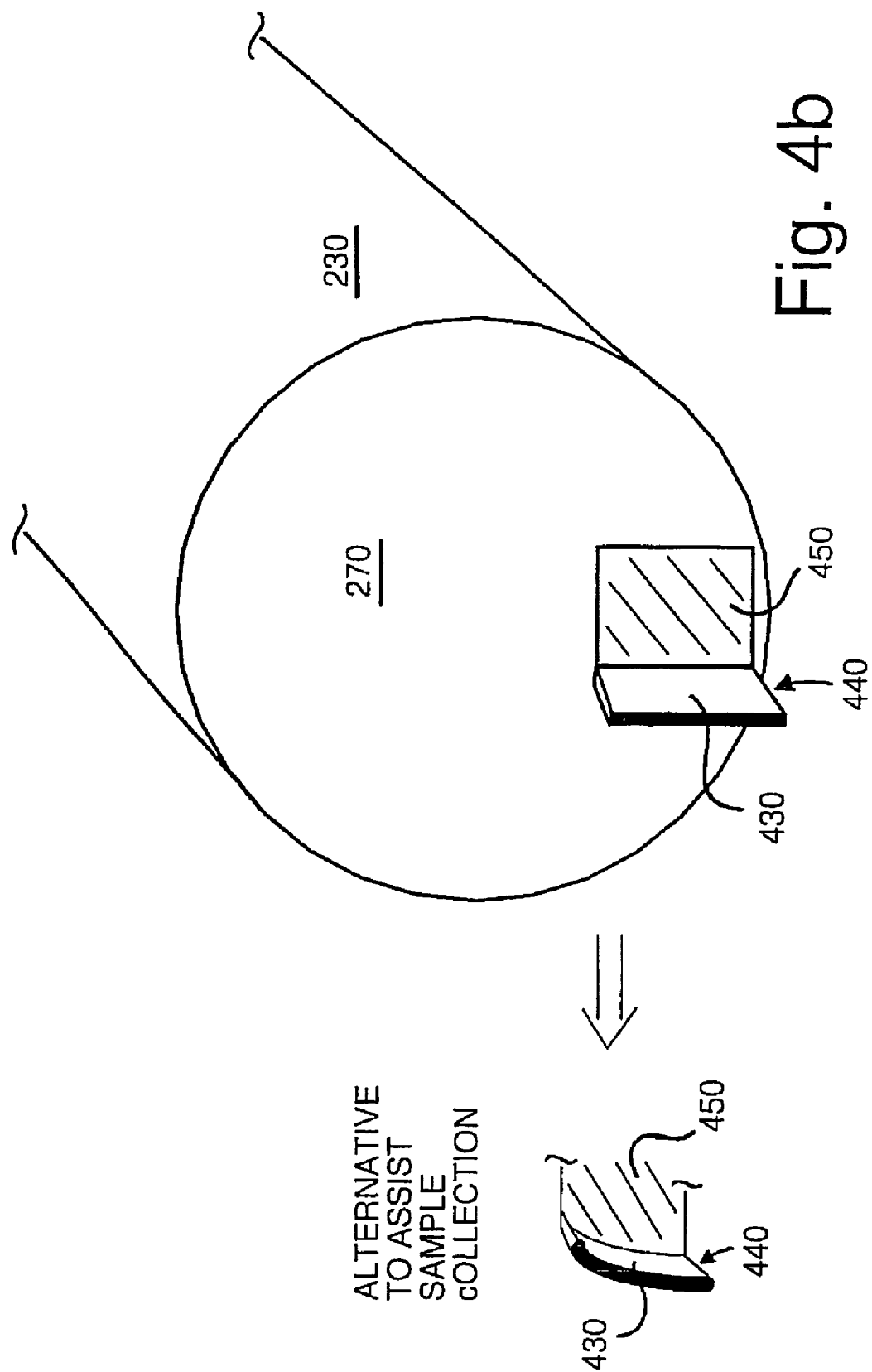

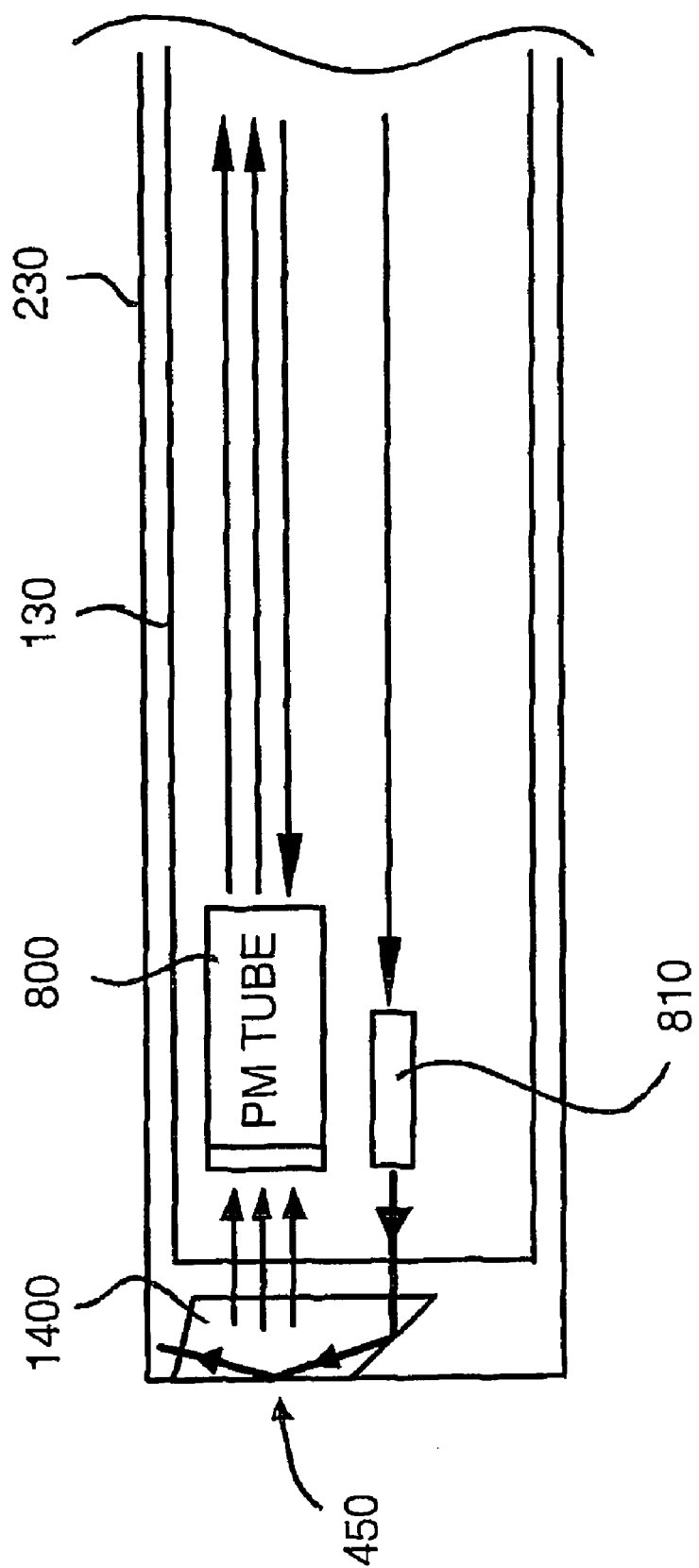

SAMPLE COLLECTION APPARATUS

This application is a Continuation-In-Part of prior application Ser. No. 10/474,877 filed Apr. 5, 2004 now U.S. Pat. No. 7,384,793.

FIELD OF THE INVENTION

The present invention relates to a sample collection apparatus; more particularly, but not exclusively, the invention relates to an apparatus for providing early detection of respiratory disease, for example tuberculosis induced by the pathogen *mycobacterium tuberculosis*.

REVIEW OF THE ART

Numerous biological measurement systems are known in the art for detecting various forms of pathogens, for example bacteria, viruses, moulds and fungi.

In an article entitled 'Detection of Antibody-Antigen Reactions at a glass-liquid interface as a Novel Optical Immunoassay Concept', Proceedings of $2^{nd}$ Optical Fibre Conference (Stuttgart 1984) pp. 75, R. M. Sutherland et al. describe an optic waveguide apparatus wherein an antibody species is covalently immobilized onto a surface of a planar or fibre-optic waveguide. A sample solution comprising an antigen is presented to the surface, whereat the antigen is immobilized by the antibody species. The antigen is interrogated using an evanescent wave component of a light beam, totally internally reflected many times within the wave-guide. The evanescent component exhibits a characteristic that it penetrates only a fraction of its wavelength into an aqueous phase at the surface whereat the antigen is immobilized; thus, the evanescent component is capable of optically interacting with substances, for example the immobilized antigen, bound to or very close to the interface and only minimally with any bulk solution which may interface onto the surface.

Moreover, in a published paper entitled 'Sensitivity enhancement of evanescent wave immunoassay' (1993) Yoshida et al. Meas. Sci. Technol. 4 pp. 1077-9, there is described a fluoro-immunosensor suitable for the detection of low concentrations of pathogens in blood and serum samples. The immunosensor employs an assay system including a sandwich assay in a flow cell. For a standard sandwich assay, a number of wash-steps are required. These wash-steps complicate the system and make it necessary for a relatively skilled operator to carry out the testing.

In a published United Kingdom patent no. GB 2174802, there is described an optic-waveguide biosensor for detecting and monitoring specific assay molecular species in flowing test fluid samples. The biosensor employs a complex multiple reflection optical geometry wherein fluorescence associated with the binding of an antigen to an antibody-coated surface is characterized by an increase in the signal detected in the same direction as that detected for the multiply reflected incident light. A disadvantage of this sensor is that bulk scattering by an optical waveguide forming a part of the sensor can affect the signal level detected at the waveguide. Moreover, multilayer construction configurations of the optical waveguide serve to further complicate the biosensor and the complexity of signal levels observed. Again, the operator of the biosensor must be relatively skilled.

In another published patent application no. GB 2227089, there is described a system for the analysis of specific assay molecular species in test fluid samples. The system employs a detection method involving the use of detection of an evanescent wave component of an antibody immobilized on the surface of a planar or fibre optic waveguide. The coupling of the resonant wavelength is facilitated by an optical grating located at either the interface between the dielectric body and the medium or between the dielectric body and the sensitized coating, which can potentially result in alignment problems. Furthermore, the light is reflected many times within the waveguide and as such the intensity observed is subject to losses due to scattering.

A European patent application no. EP 0519623 discloses an evanescent wave system comprising first and second wave propagating surfaces. The first surface is used to detect the presence of a first analyte and the second is used to indicate the presence of a second analyte and/or a reference. The system is complex and, in one embodiment, makes use of the inner and outer surfaces of the two wave propagating surfaces.

In a patent application no. EP 0239382, there is described another fibre optic based device that has a high numerical aperture and does not utilize any cladding at its contact points. The device is of a complex design which employs a beam splitter and lens system susceptible to scattering losses. Again, the device incorporates a flow cell for the interrogation of optically-detectable assays. This device is of relatively high cost and complexity.

An international PCT application no. PCT/US01/21634 concerns an apparatus and method for evanescent light fluoroassays, specifically intended for use on bodily fluids. The apparatus is designed to detect multiple spatially resolved assays to be read simultaneously using detection sensors such as a CCD camera, a photodetector, a photoarray or related sensors. Air pressure, vacuum or capillary action is used to move the sample onto an assay area of a disposable cartridge. Again, this apparatus utilizes multiple reflections and, in one embodiment, these reflections occur in a very thin film, which improves measurement sensitivity. The apparatus relies upon personnel performing tests to transfer samples onto a disposable element of the apparatus and as such is not a 'safe' method of handling pathogenic samples. Moreover, the personnel are required to be of a high skill level and the apparatus tests for multiple conditions which is not the principle performance requirement of the biological measurement system of the present invention.

A U.S. Pat. No. 5,922,550 relates to a sensitive device for the detection of immunoassays. The basis of the device is somewhat different to that of the present invention in that the sensitive device uses a predetermined pattern of analyte specific receptors that, in the presence of the pathogen, produce a diffraction pattern from transmitted or reflected light. A diffraction image thereby generated can be observed by eye or by an optical reading device.

A microassay rod and card system is described in a U.S. Pat. No. 4,673,657. The rod and card system is intended for the simultaneous detection of the presence of numerous different biologically important substances in a single small sample. The device is rapid and makes use of standard immunoassay systems that are well documented in the literature. The sample must be placed on the card system and so a safe means of collection is not provided. Moreover, the detection of multiple pathogens is not desirable in the conditions for which the measurement system of the present invention is intended.

In a U.S. Pat. No. 3,992,516, there is described a direct fluorescent antibody composition and method for the detection of *pneumocystis carinii*; the method of sample collection is not presented in the patent.

A German patent application no. DE 3932784 is concerned with a test for analysing aerosols, including fluid from respiratory passages and spittle. Exhaled breath is collected directly into a mass spectrometer or is concentrated prior to analysis by collection onto a cooled plate. Analysis by mass spectrometry leads to the determination of the molecular species present in the gas/aerosol/liquid by fragmentation of these species and the subsequent determination of their masses. Such an analysis results in a complex problem of co-addition to determine all of the molecular species present. Collection on a cooled plate is a standard technique in the literature, namely matrix isolation, and has been utilized since the 1960's. The test relies on direct measurement of the whole sample, rather than making use of a chemical/biochemical assessment method. The use of a mass spectrometer is expensive and requires the incorporation of vacuum equipment; thus this test is of high cost and is not portable.

In a United Kingdom patent application no. GB 2311856, an environmental sampler is described for recovering particles having diameters in a range of 0.1 µm to 20 µm. In the sampler, a feed is used to coat the surfaces of beads in a bead bed with liquid, which then entraps particles from an air sample. The liquid is then recovered and analysed for the components that have dissolved in the liquid. Such an assay would not be appropriate for the collection of pathogens contained within sputum/mucus from the upper lung area.

In an International PCT application no. PCT/AU95/00540, there is described a nasal/oral filter designed for particle entrapment by inhalation or exhalation. The filter comprises a collection system designed to fit into a user's mouth or nostril and has a non-linear path to capture particulates. In this filter, the main target particles for capture are potentially allergenic species, but the possibility exists to capture viruses or mycobacteria. The particles can be recovered by washing or blowing through the sample collection system and subsequently analyzed by culture, nucleic acid analysis or similar processes. Such an approach means that the sample is transferred to another system which immediately gives rise to safety issues concerning safe sample handling and speed of testing the samples.

An international PCT patent application no. PCT/SE96/00474 concerns a device that investigates one or more components of exhaled air for the presence of the pathogenic *helicobacter pylori* in the stomach and intestinal tracts of human beings. The device comprises a tubular element for conducting exhaled air onto an airtight plate incorporating a porous membrane for sample collection. Prior to producing the sample, the patient swallows an isotope-labeled, preferably radioactive, urea preparation, which breaks down in the presence of *helicobacter pylori*. The preferred embodiment of the device indicates the presence of radioactive carbon dioxide formed as a conversion product of *helicobacter pylori*. The plate absorbs the radioactive carbon dioxide and is subsequently removed from the device for radioactive analysis. In the detection of viruses and bacteria, such as *mycobacterium tuberculosis*, the device is inappropriate as there is no simple way provided to isotopically label the pathogen nor is there any simple way of forming a simple breakdown product.

In a U.S. Pat. No. 4,350,507, there is described a particle sampling apparatus for the collection of dust particles from the atmosphere. The apparatus employs a grill and pre-filter system to remove largest non-respirable particles and then a main filter to collect the respirable particles. This limits the dust concentration in some industrial situations to tolerable limits. The apparatus is not disclosed as being capable of performing biochemical assay analysis.

In a U.S. Pat. No. 5,372,126, there is described a pulmonary sampling chamber designed for the safe collection of pulmonary samples. The apparatus entirely encloses the patient and, as such, is not portable. The primary aim of the system is to collect deep sample secretions non-invasively from a patient's lungs. Moreover, the chamber is equipped with a replaceable exhaust filter unit to trap airborne pathogens and other harmful particles; the exhaust filter can subsequently be removed for analysis and disposal.

A U.S. Pat. No. 3,745,991 describes a device for reducing environmental contamination during medical treatment and/or diagnosis. The aim of the device is to safely deliver and/or collect aerosol samples from a patient by enclosing the patient's face and passing any fluids generated by exhalation from the patient through a filter system to collect any hazardous materials for later disposal/analysis. The device is not easily portable.

THE PROBLEM(S) TO BE SOLVED ACCORDINGLY

It is becoming increasingly important for organisations, for example government agencies and humanitarian relief agencies, to have at their disposal facilities for the rapid detection and identification of pathogens. Such pathogens include newly emerging viruses and re-emergence of known diseases such as bubonic plague, tuberculosis and cholera. On account of such pathogens becoming increasingly resilient to medication, there is a considerable need for measurement systems that can be used for the early detection of pathogen outbreaks so that isolation measures and targeted medication can be applied to contain further pathogen spread.

Moreover, on account of outbreaks of disease often occurring in economically less advanced regions of the world and being spread by vectors such as aviation to other regions thereof, there is a need for measurement systems which are relatively inexpensive, which are straightforward to use by untrained staff, which can give results at the point-of-test/care, and which are potentially less susceptible to inadvertently spreading pathogens when operated by untrained staff.

In particular, the detection of bacterial infection is of vital importance in global terms. Field-testing of bacterial infection, preferably using a test that responds rapidly, is particularly desirable because of the prevalence, virulence and major impact of major infections such as pneumonia, tuberculosis, malaria and other pathogens. Contemporary bacterial tests are mainly based on complex laboratory assays and are therefore potentially expensive and are not especially suitable for field use. Moreover, many contemporary tests require a substantial time period, for example in a range of 2 to 4 weeks, to provide a positive identification of the presence of pathogens. More recently, rapid tests have been developed which offer reduced identification timescales to hours/days. These rapid tests are primarily based on the analysis of sputum/mucus samples from upper lung regions; however, the collection and handling of such samples is hazardous to personnel conducting and/or supervising such testing. Thus, both timescale and potential pathogen transmission problems make these contemporary tests difficult to execute in field locations.

Furthermore, at the current state of the art for the field-testing of tuberculosis (TB), a 'standard' skin test employed is compromised by HIV status and so the only method currently used in the third world is that of smear microscopy on sputum/mucus samples. The accuracy of these tests is dependent on skilled operators and frequent re-tests.

In general, in these circumstances, a significantly safer method of pulmonary bacterial sensing is required for addressing the pathogen transmission problems that are prevalent when collecting and handling samples for subsequent pathological analysis.

Furthermore, rapid and reliable detection of other types of medical condition, for example hormonal abnormalities in the context of steroid (hormone) abuse in professional sport, markers for cancer and so on is also highly desirable.

None of the known systems reviewed above adequately addresses these problems.

SUMMARY OF THE INVENTION

In a first broad independent aspect, the invention provides a sample collection apparatus comprising:
- (a) a collector for collecting a sample comprising a collection vessel with an optical interrogation region; and
- (b) a spreader which is located on the inside of said vessel and which spreads said sample over said interrogation region.

In a subsidiary aspect, said spreader is elastically deformable.

In a subsidiary aspect, the invention further comprises marking means for optically labelling components present in the sample to produce labelled components.

In a subsidiary aspect, said marking means comprises at least one of a selective binding assay and a competitive displacement assay for optically marking the presence of the components by way of fluorescent markers; wherein said fluorescent markers are bound to antibodies for use in at least one of the selective assay and the competitive assay; wherein said fluorescent markers comprise fluorophores bound to the antibodies by way of an intermediate carrier such that a plurality of fluorophores are associated with each antibody, and wherein the intermediate carrier comprises latex spheres.

In a subsidiary aspect, the collector is arranged to enclose the sample, thereby preventing personnel contact with the sample when the system is in use.

In a subsidiary aspect, said collector is a single-use disposable part.

In a subsidiary aspect, said marking means includes lysing means for causing lysis of the components present in the sample, thereby enhancing measurement sensitivity of the system by increasing the number of available potential optical labelling sites.

In a subsidiary aspect, said vessel incorporates a lid.

In a subsidiary aspect, said lid incorporates said spreader.

In a subsidiary aspect, said apparatus incorporates a recessed portion for collection of a sample; said recessed portion having a wall incorporating an interrogation region.

In a subsidiary aspect, said vessel incorporates a lid, a body with a recessed portion for collection of a sample, and a hinge allowing the rotation of said lid relative to said body between a first position where said recessed portion is exposed to receive a sample and a second position where said lid engages said body in a non-releasable manner; whereby said recessed portion is enclosed. This will have the effect of once the lid has been shut, the tube can be safely handled and disposed of.

In a subsidiary aspect, said lid and said body incorporate a snap-fit arrangement for securing said lid against said body in said second position.

According to a further aspect of the present invention, there is provided biological measurement system for measuring the concentration of components included in a sample, the system characterised in that it comprises:
- (a) collecting means for collecting the sample;
- (b) concentrating means for spatially concentrating the sample;
- (c) marking means for optically labeling the components present in the concentrated sample; and
- (d) interrogating means for optically interrogating the labeled components and thereby generating a measure of the concentration of components present in the sample.

Preferably, the collecting means is adapted for collecting the sample in aerosol form. Aerosol sample collection is of benefit where the system is employed for testing pulmonary diseases and environmental air-borne pollutants. It maximizes the pathogen collectable by comparison with conventional (sputum-only or mucus-only) "cough"-style methods.

Preferably, the collecting means further comprises nebulizing means for emitting a mist for inducing aerosol emission from a subject. The nebulizing means is of benefit in that is capable of increasing the amount of sample obtained when performing pulmonary testing.

More preferably, the nebulizing means in use is adapted to generate a saline mist comprising saline droplets having diameters in a range of 6 μm to 20 μm. The range is of advantage in that droplet sizes of less than 6 μm is too palatable to induce coughing whereas droplet sizes greater than 20 μm can be unpleasant to inhale.

Most preferably, the saline droplets have diameters in a range of 10 μm to 15 μm and comprise saline solution having a saline concentration in a range of 0.1% to 2% by weight.

Preferably, the concentrating means further comprises a feature for scraping surfaces where the sample is deposited to spatially concentrate the sample. Spatial concentration of the sample is capable of enhancing the measurement sensitivity of the system.

Preferably, the feature is elastically deformable for spreading the spatially concentrated sample over an optical interrogation region whereat the concentrated sample is subjected to optical interrogation.

Beneficially, the marking means comprises at least one of a selective binding assay and a competitive displacement assay for optically marking presence of the components by way of fluorescent markers. Such assays are capable of providing effective interface between biochemical and optical domains.

Preferably, the fluorescent markers are bound to antibodies for use in at least one of the selective assay and the competitive assay. Antibodies, for example as employed in immunoassay, are of advantage in that they can be made highly selective with remain to molecular groupings or microbes to which they are capable of binding. Moreover, antibodies are presently becoming relative cheap to manufacture in bulk using contemporary genetic engineering processes.

Preferably, the fluorescent markers are fluorophores bound to the antibodies by way of an intermediate carrier such that a plurality of fluorophores are associated with each antibody. The use of fluorophores is of advantage in that they are capable of being excited by optical radiation at a first radiation frequency and emitting fluorescent radiation at a second radiation frequency, the first and second frequencies being mutually different, thereby enabling the excitation radiation and the emitted fluorescent radiation to be individual isolated.

More preferably, the intermediate carrier is implemented in the form of latex spheres.

The interrogating means beneficially comprises an optical evanescent detector for detecting changes in optical response induced by the presence of the components. Evanescent wave interrogation is especially advantageous as it enables a planar optical surface across which the sample is spread to be specifically targeted for interrogation.

Preferably, the evanescent detector includes:
(a) one or more of a diode laser and a LED as a source of interrogating radiation for interrogating the concentrated sample; and
(b) one or more of a avalanche photodiode, a photodiode array and a photomultiplier tube as an optical detector for detecting fluorescent radiation emitted from the concentrated sample in response to optical interrogation of the sample, the optical detector for generating a detection signal indicative of changes in fluorescence from the sample resulting from the presence of the components in the sample.

Such sources and detectors of optical radiation are of advantage in that they are potentially inexpensive, compact and robust.

Preferably, the system further comprising strobing means for strobing radiation emitted from the source of interrogating radiation, and synchronous demodulating means for demodulating the detection signal in synchronism with the strobe to render the system less sensitive to quasi-constant optical radiation received at the optical detector. Such strobing is capable of rendering the system less influenced by the effects of stray ambient illumination penetrating into the system. Moreover, such a strobe also enables effects of offset voltages within electronic components of the detecting means on the measurement to be significantly reduced.

Preferably, the system further comprising computing means for changes in the detection signal when the components in the sample are optically labeled or displace optical labels. More preferably, the computing means is arranged to monitor the concentrated sample before and after fluorescent labeling thereof to calculate the measure of the concentration of the components in the sample. Such dual measurement is of benefit in removing effects of systematic errors in the system, for example background fluorescence occurring in the interrogating means.

Beneficially, the computing means further comprises one or more of:
(a) displaying means for displaying the measure of the concentration of the components in the sample, and
(b) data logging means for storing a record of measure of the concentration of the components.

Preferably, the collecting means is arranged to enclose the sample, thereby preventing personnel contact with the sample when the system is in use. Such containment is of advantage in assisting to prevent the spread of dangerous pathogens and also renders the system safer in use.

More preferably, the collection means is arranged to be a single-use disposable part. Such single-use is of further advantage in preventing the spread of potentially dangerous pathogens. Most preferably, the collecting means comprises features rendering it substantially undismantleable after sample collection therein.

Preferably, the collecting means comprises vortex enhancing means for deposition of the sample within the collecting means.

The collecting means preferably comprising filtering means for at least partially inhibiting spread of the components of the sample from the collecting means. Preferably, the marking means includes lysing means for causing lysis of the components present in the sample, thereby enhancing measurement sensitivity of the system by increasing the number of available potential optical labeling sites.

The system according to the above aspect is capable of being used in a wide range of applications not limited to the biological domain. In particular, but not exclusively, the system is preferably adapted to identify the components in the form of one or more of the following:
(a) antibodies;
(b) nucleic acids;
(c) enzymes and/or other proteins;
(d) analogues of one or more of (a) to (c); and
(e) a microorganism.

With regard to microorganisms, the system is especially appropriate for the detection of one or more of the following:
(a) a virus;
(b) spores;
(c) molds;
(d) pollen; and
(e) a microbiological allergen.

Moreover, the system is also preferably adapted to identify the components in the form of one or more of the following:
(a) toxic dust;
(b) an explosive;
(c) a drug; and
(d) a pollutant.

According to a further aspect of the present invention, there is provided a method of detecting one or more pathogens in one or more samples of sputum from a subject using a system according to the first aspect of the invention, the method involving the steps of:
(a) collecting said one or more samples in the collecting means;
(b) spatially concentrating the one or more samples in the concentrating means;
(c) optically labeling one or more pathogens present in said one or more samples;
(d) optically interrogating the pathogens to achieve an optical response; and determining from the optical response of said one or more samples whether or not said one or more pathogens are present in said one or more samples.

Preferably, in steps (b) and (c), a fluorescently labeled assay is employed to provide the optical response.

Preferably, in steps (b), (c) and (d), detection of fluorescence is performed using evanescent-wave spectroscopy.

Preferably, when executing the method, said one or more pathogens comprise one or more of:
(1) antibodies;
(2) nucleic acids;
(3) enzymes or other proteins;
(4) analogies of (1) to (3); and
(5) a micro-organism.

The method is advantageously adapted for the detection of bacteria associated with pulmonary and pulmonary-related infections.

Moreover, the method is preferably adapted for the detection of one or more of the following pathogens:
(1) a virus;
(2) a protein and/or antibody;
(3) another symptomatic particle not included in (1) or (2);
(4) a spore;
(5) a mold;
(6) pollen;
(7) an allergen;
(8) toxic dust;
(9) an explosive;
(10) a drug; and
(11) a pollutant.

Preferably, to enhance aerosol generation, the inhalation of one or more of:
esters, water vapor, saline vapor, expectorant and menthol is used to assist release of bacteria-containing mucus from the trachea or from the upper lung of a subject being tested.

Beneficially, a partial negative pressure is employed to assist in obtaining said one or more samples in aerosol form.

The method is capable of being applied to testing a diverse range of samples. For example, said one or more samples preferably comprise an aerosol of blood or other bodily fluid or bodily fluid in liquid form.

In the method, analysis of said one or more samples is performed using one or more of:
- (a) an ELISA chromogenic reaction; and
- (b) a surface acoustic wave (SAW) biosensor to detect an antigen in said one or more samples According to a third aspect of the present invention, there is provided a sample collection apparatus or collecting aerosol samples, characterised in that the apparatus comprises:
- (a) collecting means for collecting the sample; and
- (b) concentrating means for spatially concentrating the sample.

Preferably, the collecting means further comprises nebulizing means for emitting a mist for inducing aerosol emission from a subject.

Preferably, the nebulizing means in use is adapted to generate a saline mist comprising saline droplets having diameters in a range of 6 µm to 20 µm.

More preferably, the saline droplets have diameters in a range of 10 µm to 15 µm and comprise saline solution having a saline concentration in a range of 0.1% to 2% by weight.

Beneficially, the concentrating means further comprises a feature for scraping surfaces where the sample is deposited to spatially concentrate the sample.

Preferably, the feature is elastically deformable for spreading the spatially concentrated sample over an optical interrogation region whereat the concentrated sample is subjected to optical interrogation.

Preferably, the apparatus further comprises an interrogation region whereat the sample in spatially concentrated, the interrogation region being susceptible to optical interrogation.

Preferably, the interrogation region is susceptible to evanescent wave interrogation.

Preferably, the collecting means is arranged to enclose the sample, thereby preventing personnel contact with the sample when the apparatus is in use.

To reduce the potential spread of dangerous pathogens, the collecting means preferable comprises features rendering it substantially undismantleable after sample collection therein.

Preferably, the collecting means comprises vortex enhancing means for deposition of the sample within the collecting means. Vortex enhancing means include one or more of a septum and a bend in a sample collection region.

To reduce the risk of spreading potentially dangerous pathogens, the collecting means preferably comprises filtering means for at least partially inhibiting spread of the components of the sample from the collecting means According to a further aspect of the present invention, there is provided an immunosensor for collecting one or more samples of sputum from a patient in the form of an aerosol and for analysing said one or more samples to detect whether or not pathogens are present therein.

The immunosensor is capable of providing a significantly safer method of pulmonary testing, the sensor being designed for safe handling of test samples.

Preferably, in the immunosensor, said one or more samples are in solution within the sensor and detection of the pathogens within said one or more samples is performed using a fluorescently labeled assay. The fluorescently labeled assay is capable of providing a sensitive and reliable approach to detecting presence of the pathogens.

More preferably, the detection of bacterial pathogens is performed using evanescent-wave spectroscopy or fluorimetry. The use of evanescent-wave spectroscopy or fluorimetry enables optical interrogation to be applied efficiently to a relative small sample of pathogen to detect its presence.

Preferably, the immunosensor is adapted to detect one or more of the following pathogens:
- (a) antibodies;
- (b) nucleic acids;
- (c) enzymes and/or other proteins;
- (d) analogues of one or more (a) to (c); and/or
- (e) a micro-organism.

More preferably, the immunosensor is adapted for the detection of bacteria in a sample, the bacteria being associated with pulmonary and pulmonary-related infections. Alternatively, or additionally, the immunosensor is adapted for the detection of one or more of:
- (a) a virus;
- (b) a protein and/or antibody;
- (c) other symptomatic particles not included in (a) and (b); for example indicators of forms of cancer.
- (d) spores;
- (e) molds;
- (f) pollen;
- (g) an allergen;
- (h) toxic dust;
- (i) an explosive;
- (j) a drug; and
- (k) a pollutant.

According to a further aspect of the present invention, there is provided a method of detecting one or more pathogens in one or more samples of sputum from a patient using an immunosensor according to the fourth aspect of the invention, the method involving the steps of:
- (a) collecting said one or more samples in the immunosensor;
- (b) fluorescently labeling one or more pathogens present in said one or more samples;
- (c) interrogating said one or more samples using optical interrogation to achieve an optical response; and
- (d) determining from the optical response of said one or more samples whether or not said one or more pathogens are present in said one or more samples.

Preferably, in steps (b) and (c), a fluorescently labeled assay is employed to provide the optical response.

More preferably, for efficiently interrogating a relatively small quantity of sample detection of fluorescence in steps (b), (c) and (d) is performed using evanescent-wave spectroscopy or evanescent-wave fluorimetry.

Preferably, the method is susceptible to detecting the occurrence of said one or more pathogens by way of:
- (1) antibodies;
- (2) nucleic acids;
- (3) enzymes or other proteins;
- (4) analogies of (1) to (3); and
- (5) a microorganism.

More preferably, the method is adapted for the detection of bacteria associated with pulmonary and pulmonary-related infections.

Alternatively, or additionally, the method is preferably adapted for the detection of one or more of the following pathogens:
- (1) a virus;
- (2) a protein and/or antibody;
- (3) another symptomatic particle not included in (1) or (2);
- (4) a spore;
- (5) a mold;

(6) pollen;
(7) an allergen;
(8) toxic dust;
(9) an explosive;
(10) a drug; and
(11) a pollutant.

In order to induce more efficient sample generation, the method preferably involves the inhalation of one or more of: esters, water vapor, saline vapor, expectorant and menthol to assist release of bacteria-containing mucus from the trachea or from the upper lung of the patient. The patient, in this case, may be either a human being or an animal.

Inhalation of the vapor should be from a separate vessel such as, but not exclusively, a simple nebuliser, from within the sample collection system or via an inlet tube to the sample collection system. Inhalation may take place via a pipe which may or may not incorporate a demand valve, diaphragm valve or similar.

Exhalation may be via a 'plug' in the pipe that ruptures to allow 'breath' to enter the chamber and activate the fluorophore marked antibody.

The sample is collected directly onto a prism in the sample collection system.

Exhalation by the patient is via a large inlet pipe. The aerosol exits the sample collection system via a smaller diameter pipe, into a filter or sample collection bag. The effect of the two different diameters is the creation of a 'swirl' effect in the vessel.

Exhalation into the sample collection vessel may be via a plug that ruptures to release a hydrating agent, such as PBS or water, and/or the desired antibodies and/or fluorescent markers into the sample collection vessel. Further, exhalation into the sample collection vessel may be via a pipe or pipe containing a venturi. The exit pipe of the sample collector may also incorporate a venturi.

A partial negative pressure may be employed to assist in obtaining said one or more samples in aerosol form.

Preferably, said one or more samples comprise an aerosol of blood or other bodily fluid, such as urine, pathogenic sera, semen, saliva, tears or sweat. The analysis of these fluids significantly increases the range of pathogens that can be tested. Tests on saliva can, for example, be carried out to detect *streptococcus* and *staphylococcus*.

The method is preferably adapted to analyse one or more samples of non-biological origin.

The interrogation technique is also adapted for use to detect all of the pathogens described above, with liquid samples of bodily fluids such as blood, urine, pathogenic sera, semen, saliva, tears or sweat and other samples such as food and non-biological samples.

The samples, either in the form of aerosol or liquid, may be diluted using PBS, water or other appropriate solvent.

The method is preferably adapted to cope with particles of non-biological origin including at least one of an environmental aerosol and an effluent.

More preferably, analysis of said one or more samples is performed using one or more of:
(a) an ELISA chromogenic reaction; and
(b) a surface acoustic wave (SAW) biosensor to detect an antigen in said one or more samples.

Preferably, the sensor is used to execute a test which analyses exhaled breath, which is in the form of an aerosol, comprising bacteria or other pathogens to be detected contained in water or sputum droplets of such breath. The aforesaid one or more samples are preferably collected directly into a sample tube for testing using, for example, a fluorometric assay.

Hydration, using PBS, water or other suitable solvent may be required in order to differentiate between bulk and surface fluorophores.

A fluorometric assay technique may require time for culture to increase the sample numbers to aid detection.

Preferably the sample collection system will be shatterable or splinterable after use for safe disposal after a single use.

Fluorimetry has been shown to be of considerable importance for the detection of biological materials such as proteins and DNA, where fluorophores on antibodies are used as markers for detection. Detection using such fluorimetry can be executed by way of either:
(a) bulk fluorescence measurements; or
(b) through the application of interrogation techniques such as evanescent wave detection; or
(c) cavity ring down spectroscopy; or
(d) through the use of displacement assays.

Such fluorimetry offers some potential advantages in terms of specificity, simplicity, and sensitive. Evanescent wave detection is well known, but low-cost evanescent wave fluorimeters are not yet commercially available for use in pathogen detection as described with respect to the present invention.

The inventors are unaware of prior art regarding developments on the detection of pulmonary bacterial infectious agents from exhaled breath using fluorimetry. The present invention represents an improvement over exiting techniques because it reduces the level of expertise required to carry out an assay test; moreover, hazard associated with potential transmission of diseases to the tester from handling contaminated samples is reduced. The inventors have therefore devised an immunosensor which is fast acting, low cost, and portable with disposable sample holders; the immunosensor is especially susceptible to use in field environments, for example in third-world countries. It is designed for screening large patient numbers and retesting as appropriate in for example, schools and institutions.

In a further aspect of the present invention, there is provided a sample collection apparatus comprising:
(a) a sample collection volume bounded by an interior surface for receiving a gaseously-borne sample;
(b) A sample collection volume bounded by an interior surface for receiving a liquid sample where the liquid is sprayed into or added dropwise into the sample collector, and
(c) collecting means for collecting, in use, at least a portion of the sample deposited on the interior surface and for concentrating the portion at a test location susceptible to subsequent interrogation.

The invention is of advantage in that the apparatus is capable of effectively and conveniently collecting the sample for analysis.

Preferably, the collection volume is provided with vortex generating means for causing, in use, an incoming jet transporting the gaseously-borne sample to form into one or more vortices to assist with deposition of the sample onto said interior surface.

Vortex flow in a fluid carrying a particulate load results in conversion of kinetic energy in the flow to thermal dissipation therein and a subsequent deceleration with a resulting deposition of the particulate load transported within the flow.

Preferably, the collection volume is implemented as a tubular element and the collecting means is implemented as a plunger element arranged to slidably engage within the interior surface of the tubular element. Such an arrangement is of advantage in that the tubular element is convenient for offering to users' mouths and for hand-held support, whereas the plunger element is capable of sealing an end of the tubular element and, when pushed into the tubular element, assisting to spatially concentrate the sample.

More preferably, the plunger element forms a sufficient seal onto the tubular element for collecting the sample into a ring-like mass when the plunger element, in use, is slidably moved within the tubular element.

Preferably, the plunger element includes an end region comprising a projection susceptible to collecting the ring-like mass together when the plunger element is rotated relative to the tubular element. The projection is capable of functioning in a spoon-like manner to scoop up the sample from the tubular element to concentrate it into one spatial location.

The plunger element advantageously includes at its end region, optical interfacing means for interfacing between optical interrogating means and the sample, thereby enabling the optical interrogating means to interrogate the sample via the optical interfacing means. Use of optical interrogating means is of benefit in that non-contact interrogation of the sample can be achieved, thereby, in the case of contagious pathogens, reducing the risk of spreading disease further.

Preferably, the plunger element comprises a hollow interior region for receiving, in use, the optical interrogating means. Concentric mounting of the interrogating means within the plunger element, and concentric mounting of the plunger element within the tubular element is of benefit in enabling the interrogating means to be brought in close proximity, for example within a few mm, of the sample. Moreover, such concentric mounting also renders the apparatus potentially highly compact.

Preferably, the tubular element and the plunger element are designed to be disposable items whereas the optical interrogating means is designed to be a non-disposable item. Such disposability is of advantage when the tubular element and the plunger element are used to collect samples including pathogens that are potentially contagious; the tubular element and the plunger element can, for example, be disposed of by incineration to circumvent spread of undesirable pathogens. More preferably, the tubular element and the plunger element are designed to be mutually interlocking after sample collection has occurred therein to prevent these elements being reused with associated risk of cross-contamination.

The optical interfacing means preferably comprises a prism for guiding interrogating radiation from the interrogating means to the sample, and for guiding response radiation from the sample back to the interrogating means. Use of a single optical component for bi-directional optical radiation propagation enables the cost and size of the apparatus to be potentially reduced. More preferably, the prism is a dove-type prism; such a prism is susceptible to being used, for example, in evanescent-wave optical interrogation of samples, especially samples subjected to fluorophore tagging.

The interrogating means comprises a source of strobed radiation for providing the interrogating radiation, and a photodetector and associated demodulator for detecting response radiation from the sample and for demodulating the response radiation with respect to the strobe. Such a strobe arrangement can be applied to discriminate ambient quasi-constant optical radiation contributions, for example as a result of light leakage into the apparatus from its ambient environment.

Preferably, for ease and cheapness of manufacture, one or more of the tubular element and the plunger element are fabricated from plastics materials. More preferably, the plastics materials comprise one or more of an acrylate, polyethylene, polypropylene, silicone rubber, polyvinyl chloride (PVC), alkylene, polycarbonate, and polytetrafluoroethylene (PTFE) plastics material. Most preferably, the plastics materials are injection moulded.

According to a further aspect of the invention, there is provided a method of collecting a sample from a user utilizing an apparatus according to the first aspect of the sample collection system, the method comprising the steps of:
(a) exhaling mucus droplet borne air from the user into a collection volume of the apparatus;
(b) depositing mucus droplets from the exhaled air onto an interior surface of the collection volume;
(c) collecting the droplets together from the surface using collecting means of the apparatus to provide a collected mass of droplets.

Preferably, the method further comprising the step of interrogating the collected mass of droplets after step (c) to determine one or more characteristics thereof. More preferably the collected mass is interrogated optically.

Preferably, in the method, the collected mass is arranged to fluoresce in response to being optically interrogated, and the one or more characteristics determined from the fluorescence.

Preferably, in step (b) of the method, the exhaled air is arranged to flow in vortices to promote deposition of the droplets onto the interior surface.

It will be appreciated that features of the invention described in the foregoing can be combined in any workable combination falling within the scope of the invention as defined by the final claims.

DESCRIPTION OF THE DRAWINGS

Embodiments of the invention will now be described, by way of example only, with reference to the following diagrams in which:

FIGS. 4a to 4c are illustrations of a plunger suitable for use with the collection tube of FIG. 3;

FIGS. 8a and 8b are illustrations of optical components included within the electronics module of FIG. 5;

FIG. 18a shows a perspective view of a sample collection apparatus prior to engagement with an interrogation apparatus.

FIG. 18b shows the sample collection apparatus in engagement with the interrogation apparatus as previously illustrated in FIG. 18a.

DESCRIPTION OF EMBODIMENTS OF THE INVENTION

In the following description, embodiments of a biological measurement system will initially be described in overview. Later, component parts of the embodiments and their associated biochemistry will be described in more detail.

The system described herein employs evanescent wave spectroscopy and evanescent wave fluorimetry to detect the presence of a pathogenic substance using an immunoassay technique.

1. System Overview

Figure 1:
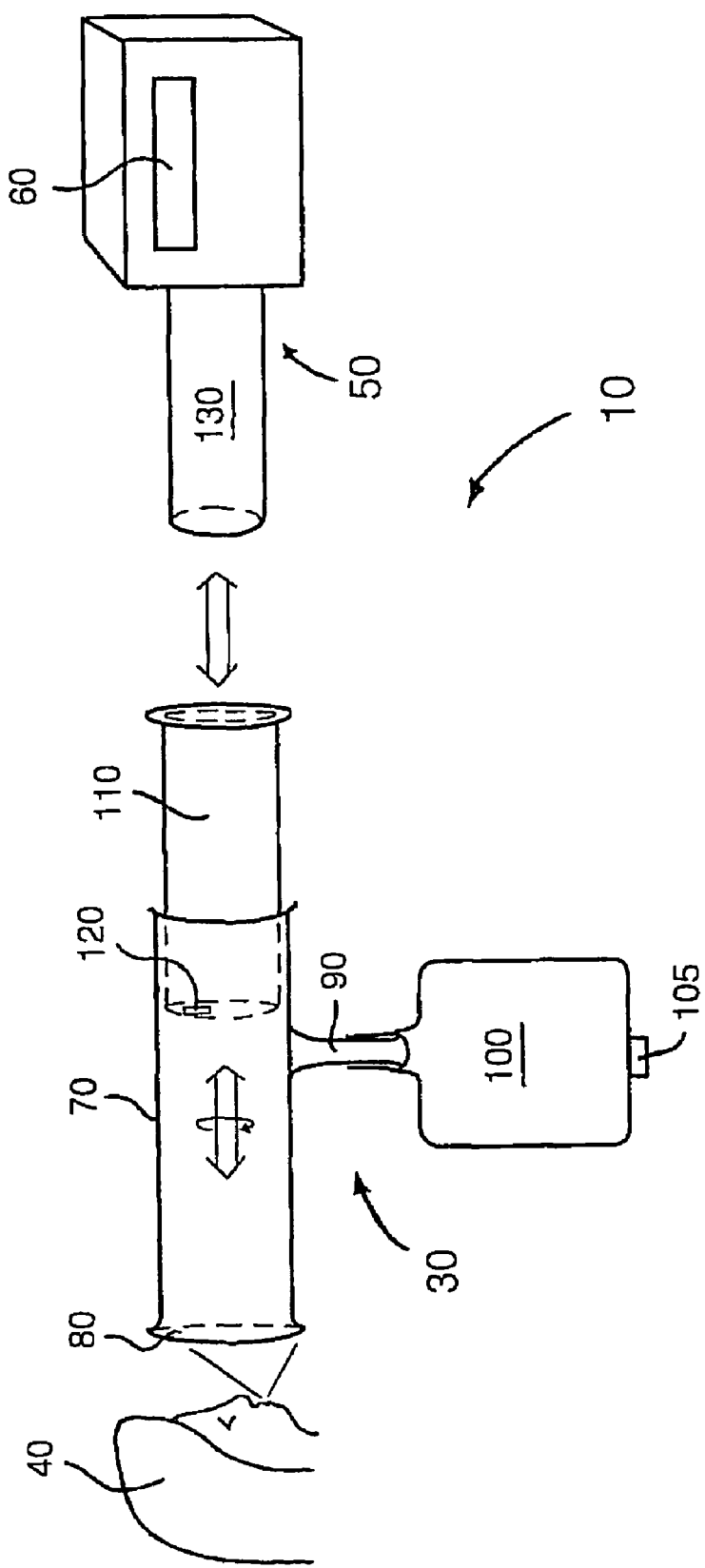
FIG. 1 is a schematic diagram of a biological measurement system according to the invention.

Referring firstly to FIG. 1, there is shown a biological measurement system according to the invention. The system is indicated generally by 10 and comprises a sample collection unit indicated by 30, and a corresponding complementary reader unit indicated by 50. For displaying test results, the reader unit 50 includes a readout display 60. The collection unit 30 is adapted for collecting exhaled material from a user 40, such material providing test samples for subsequent analysis.

The collection unit 30 is designed to engage mechanically into the reader unit 50. Moreover, the collection unit 30 is sufficiently compact for it to be hand-held by the user 40. Furthermore, the collection unit 30 is implemented in the form of a hollow sample tube 70 comprising:

(a) an input orifice 80 for engaging onto a mouth region of the user 40;
(b) an intermediate orifice 90 for coupling to a gas collecting region, for example to an inflatable bag 100; and
(c) an access orifice for a piston-like plunger 110 which is slidably and rotationally moveable within the sample tube 70.

In order to reduce a risk of cross-contamination from one user to another, the collection unit 30 is designed to be a disposable item; namely, the collection unit 30 is used only once to collect the sample for testing and to safely present the sample to the reader unit 50 for interrogation. The collection unit 30 is preferably molded from a plastics material to render it relatively inexpensive to manufacture, and also to render it susceptible to incineration to reduce the spread of potentially dangerous pathogens collected therein. Moreover, the collection unit 30 is designed so that the reader unit 50 is prevented from coming into direct contact with collected samples within the tube 70 which can potentially comprise dangerous pathogens.

2. Overview of System Operation

Figure 2:
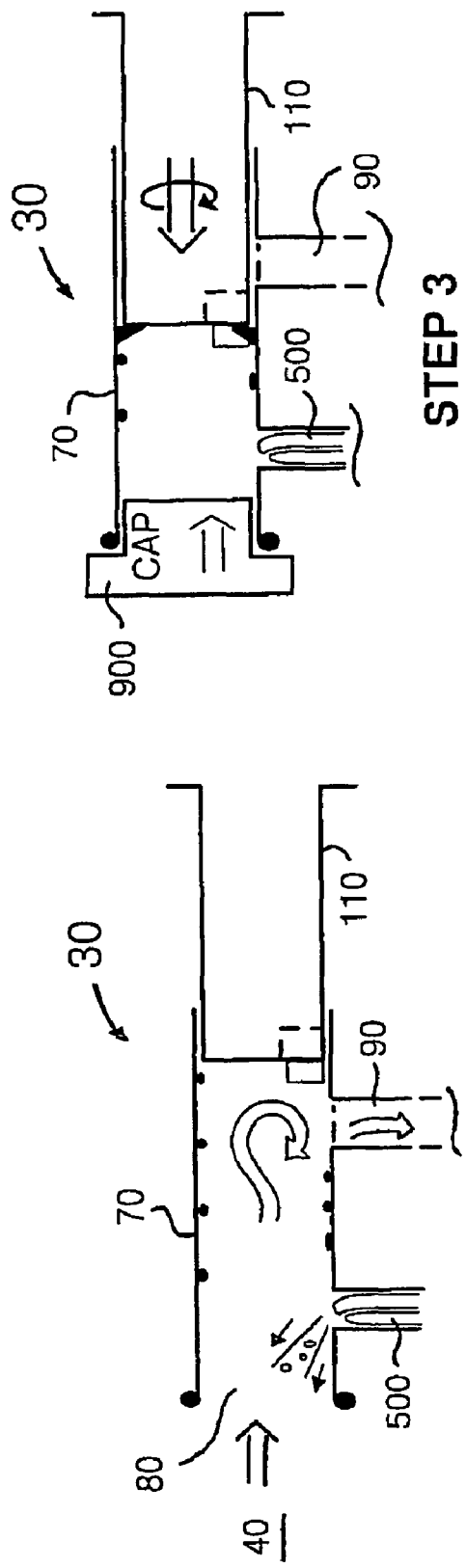
FIG. 2 is a schematic illustration of operation of a sample collection unit of the measurement system of FIG. 1.
Figure 2:
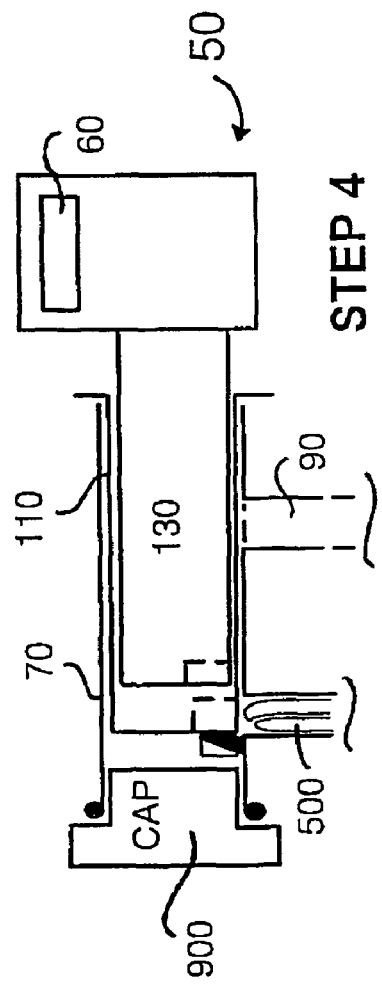

Operation of the biological measurement system 10 will now be described in overview with reference to FIGS. 1 and 2.

After manufacture including the deposition of active biomaterials, the collection unit 30 is preferably sealed within a desiccated hermetically-sealed package for storage prior to deployment. Such a package potentially prevents moisture from denaturing the aforementioned active biomaterials and also potentially reduces the risk of the collection unit 30 unintentionally becoming contaminated with pathogens prior to use; thus, such a package assists to prevent the system 10 from yielding unrepresentative test results.

Step 1: Immediately prior to deployment, the user 40, or a person supervising testing, removes the collection unit 30 from its hermetic package. The user 40 then engages his/her mouth to the input orifice 80 of the sample tube 70.

Step 2: Next, if required to assist in the production of a sample from the user 40, a saline mist is generated either from within the sample tube 70, for example from a miniature pressurized gas canister atomizer coupled thereto, or within a nebulising device remotely connected to the collection unit 30; conveniently, the nebulising device is a foot-operated pump-like device. The user 40 inhales the saline mist via the input orifice 80, the mist inducing sufficiently vigorous coughing for the user 40 to exhale sputum and/or mucus in the form of an aerosol through the orifice 80 into the sample tube 70. The aerosol passes into the tube 70 and is encouraged by the aerodynamic internal profile of the tube 70 to circulate and decelerate in a vortex-like trajectory to deposit mucus and/or sputum onto internal walls of the tube 70. Preferably, a collection volume, for example the inflatable bag 100 of plastics material such as polyethylene or polyvinyl chloride (PVC), connected to the intermediate orifice 90 is included to receive air exhaled by the user 40; each cough can amount to two liters volume of air, hence the bag 100 is conveniently sized to accommodate several coughs. More preferably, the collection bag 100 is provided with an gas exit orifice 105 comprising a fine filter having a pore size which is sufficiently large to enable the bag 100 to deflate over a period of several tens of seconds, thereby rendering the bag 100 subsequently convenient in size to handle when deflated, but also sufficiently small to substantially prevent spread of potential pathogens exhaled by the user 40. Moreover, the intermediate orifice 90 is of moderate flow resistance relative to the input orifice 80 and exit orifice 105 and is preferably included between the sample tube 70 and its associated bag 100 so as to enhance the aforesaid vortex gas trajectory and promote efficient deposition of mucus and/or sputum within the sample tube 70.

Alternatively, a sample of saliva can be collected from the test subject via the action of spitting into the sample collection apparatus.

Step 3: When a sufficiently large sample of sputum and/or mucus is collected within the collection unit 30, a sealing cap (not shown in FIG. 1, but denoted by 900 in FIG. 2) is placed over the input orifice 80. Next, the plunger 110 is actuated to mechanically concentrate the sputum and/or mucus within an interrogation region, for example an optical surface 120 of the plunger 110; in particular, the sputum and/or mucus is concentrated onto the optical interrogation surface 120 provided at an end face of the plunger 110, the optical surface 120 being capable of supporting evanescent interrogation-radiation propagation which will be described in more detail later. Preferably, the plunger is both pushed and rotated within the sample tube 70 to mechanically concentrate the test sample at the surface 120. More preferably, the plunger 230 is rotated by at least 360° to ensure that as much of the sample as possible is collected onto a sample collection projection of the plunger.

An incubation period may be needed prior to optically interrogating the sample to generate a measurement reading.

Step 4: When the plunger 110 has been pushed substantially fully into the sample tube 70 to fully collect the sample onto the optical surface 120, the collection unit 30 is then offered to the reader unit 50 so that a projection 130 thereof couples into the plunger 110 to enable optical interrogation of the optical surface 120 for determining optical properties of the sample thereat; such optical interrogation is preferably achieved by way of evanescent light propagation at the surface 120. Results of the optical interrogation are presented on the display 60 to the user 40 and/or associated tester to establish whether or not the user 40 is infected with one or more pathogens, for example *mycobacterium tuberculosis*, to which the system 10 is responsive.

This completes an overview of operation of the system 10.

One or more of the sealing cap, the collection tube 70 and its plunger 110 can have incorporated therein one or more reservoirs of liquid for treating the optical surface 120 prior to optical interrogation thereof. Such puncturable reservoirs preferably contain buffer solutions or reagents such as, but not exclusively:

(a) lysing agents for causing collected pathogens, for example mycobacterium, to fragment;
(b) rinsing agents for rinsing displaced fluorophores from the optical surface 120 and/or flooding the optical surface 120 in fluorophores coupled to pathogen-selective antibodies;
(c) thinning agents to break up mucus; and
(d) developing agents for the sample such as labeled antibodies.

Reagents may be in the form of solids such as a lyophilized sphere to protect them during storage; such solid reagents may be present in one or more reservoirs or in the sample collection tube 70.

These one or more reservoirs are preferably arranged to be user puncturable to deliver their contents after sample collection but prior to optical interrogation. Mechanical construction of the reservoirs will be described later with reference to FIG. 9.

As will be further described later, the optical surface 120 is one optical face of a prism configured to support evanescent light radiation propagation therealong. The prism is preferably implemented as a dove prism, although alternative types of prism can be employed.

3. System Component Parts

Detailed design of individual components of the system 10 will now be described.

3.1 Sample Collection Unit

Figure 3:
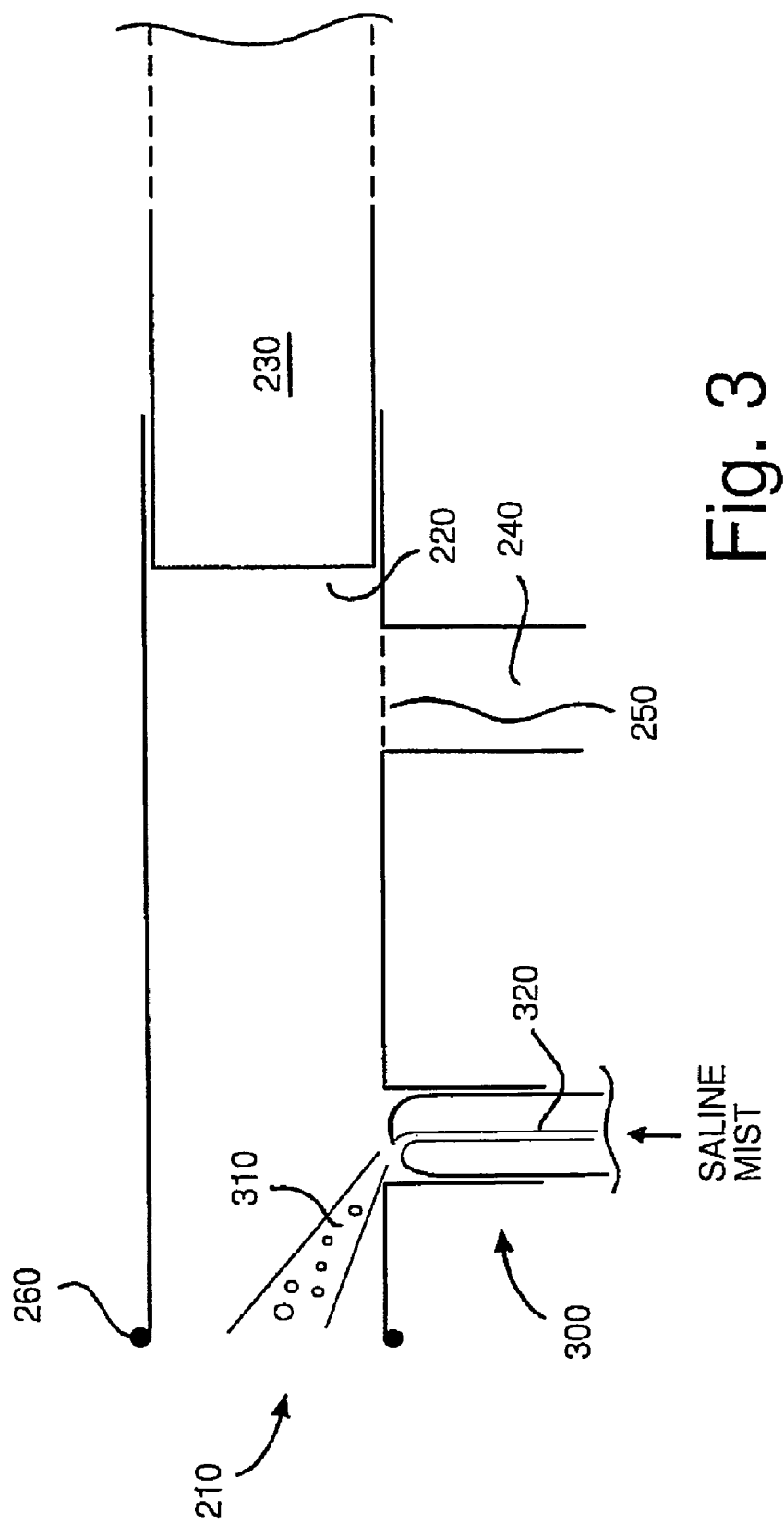
FIG. 3 is an illustration of a sample collection tube of the measurement system of FIG. 1.

Referring next to FIG. 3, there is shown the hollow sample tube 70 implemented as a substantially cylindrical hollow sample tube 200. The tube 200 comprises a first open end indicated by 210 for receiving an exhaled sample from the user 40; the first open end 210 corresponds to the input orifice 80 in FIG. 1. Moreover, the tube 200 further comprises a second end 220 for receiving a hollow plunger 230; the plunger 230 corresponds to the plunger 110 of FIG. 1. The tube 200 also includes a substantially cylindrical side tube 240 serving as the intermediate orifice 90, the side tube 240 having an associated longitudinal central axis substantially orthogonal to that of the sample tube 200. At a region where the tubes 200, 240 adjoin, there is preferably included a mesh or filter gauze 250. The tube 200 further comprises a peripheral ring 260 around the first end 210 so that this end 210 is substantially devoid of any sharp edges which could injure the user 40 manipulating the tube 200, for example when the user 40 manipulates the tube 200 towards his/her mouth.

The hollow plunger 230 is also of substantially cylindrical form and fabricated to be slidably and rotationally moveable concentrically within the inside of the sample tube 200 as illustrated, the tube 200 and the plunger 230 being a mutually precise fit. Preferably, the plunger 230 is provided with a resiliently deformable sealing ring (not shown) substantially at an end of the plunger 230 offered to the sample tube 200 when in use. The sealing ring is preferably fabricated from a nitrile rubber material, for example proprietary Viton material, silicone or polytetrafluoroethylene (PTFE). Moreover, the sealing ring is advantageously devoid of any lubricating material, for example silicone grease, which could potentially contaminate samples collected within the tube 200, and thereby compromise system 10 operation. Additionally, vapor emitted from a lubricant may potentially be harmful to the user 40 if ingested.

The hollow tube 200 is additionally provided with a saline atomizing assembly indicated generally by 300 at a region of the tube 200 near to the first open end 210. The assembly 300 is preferably coupled to a nebulizer, for example a foot-pump operated device, for forcing saline solution at pressure to the assembly 300 for generating a divergent jet 310 of saline mist for inhalation by the user 40; the saline mist is effective at promoting vigorous coughing to induce user 40 ejection of sputum and/or mucus. Preferably, the jet 310 comprises saline droplets having a diameter in a range of 6 μm to 20 μm. More preferably, the saline droplets have a diameter in a range of substantially 10 μm to 15 μm. A saline solution from which the droplets are generated preferably is of a concentration in a range of 0.1% to 2% by weight of sodium chloride to water; more preferably, the saline solution is of a concentration in a range of 0.7% to 1.1% by weight. The assembly 300 includes a substantially central capillary tube 320 which is angled at its nozzle end towards the first open end 210 to reduce an amount of saline mist swept towards the plunger 230. Preferably, the assembly 300 is recessed relative to the inside bore of the hollow tube 200 so that the plunger 230 can be advanced towards the first end 210 beyond a region where the assembly 300 is connected to the hollow tube 200 as illustrated. The assembly 300 is preferably integrally molded as part of the hollow tube 200; alternatively, in order to simplify molding tools required, the assembly 300 can be a snap-fit retained insert which is assembled into a projecting side port of the hollow tube 200 during manufacture. If required, the side port can be molded with its central axis orientated towards the first end 210 so that the insert does not require its capillary tube 320 to be shaped towards this end 210.

Induction of more efficient sample generation may alternatively be accomplished by the inhalation of one or more of water vapor, esters, expectorant and/or menthol.

Figure 4C:
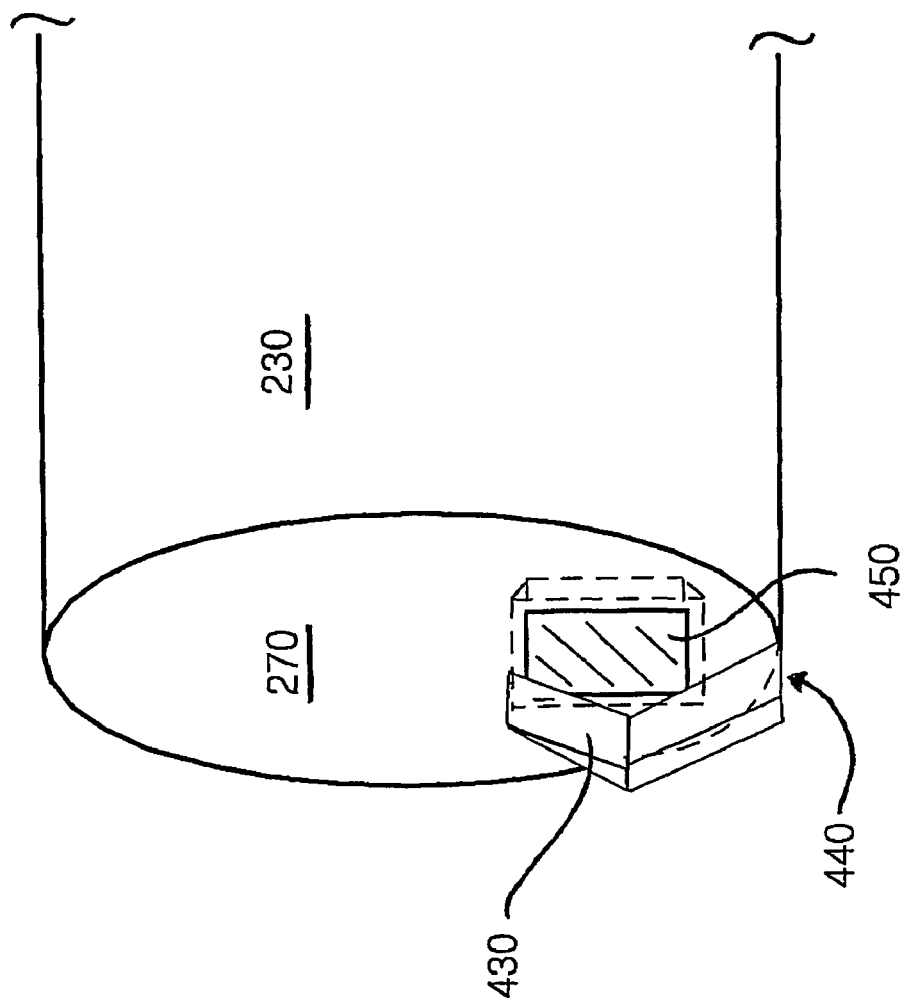
Figure 5:
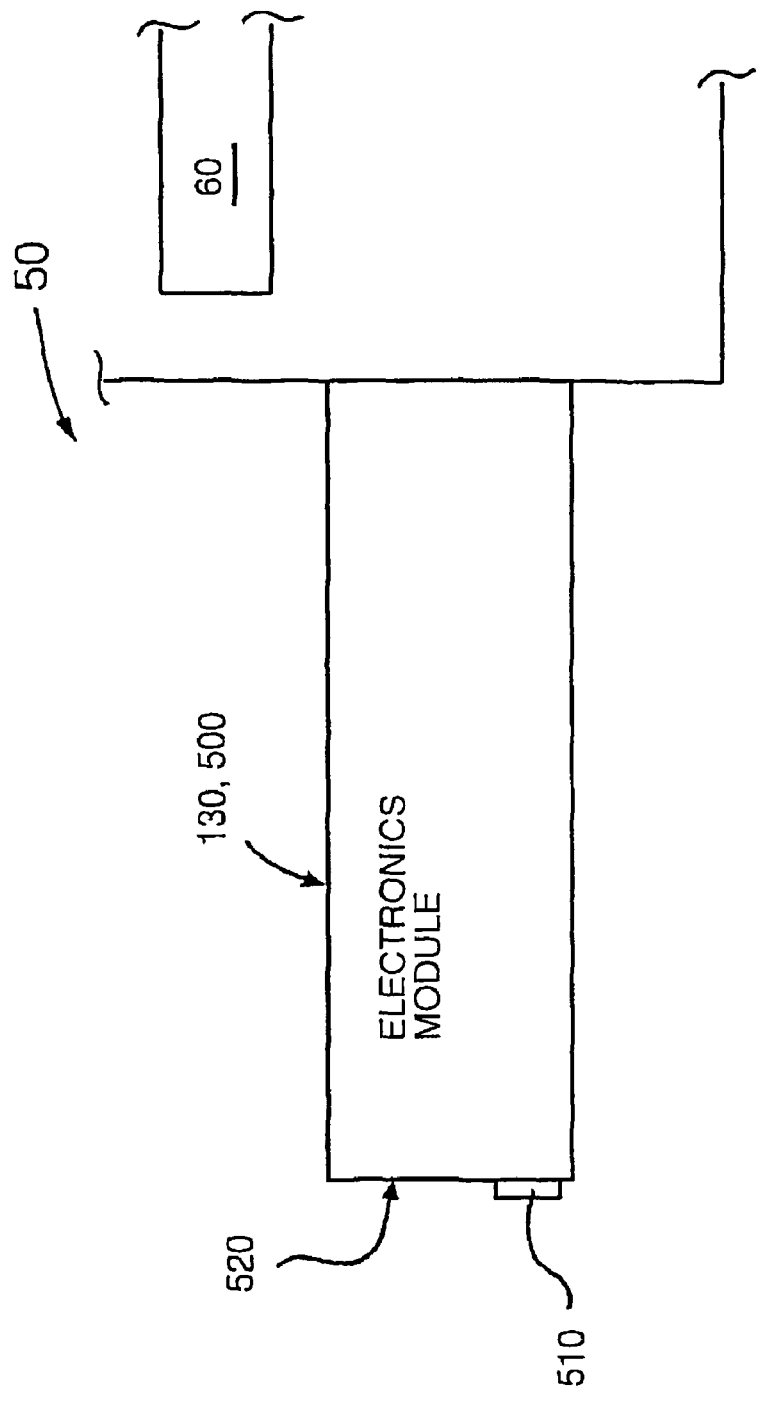
FIG. 5 is an illustration of an electronics module of a reader unit of the measurement system of FIG. 1.

In operation, the plunger 230 is retracted so that its end surface indicated by 270 in FIG. 4 is substantially at the second end 220 of the tube 200. In such a collecting state, the tube 200 has most of its interior surface, preferably in excess of 80% thereof, exposed to the first end 210. Moreover, in the collecting state, a route for gas flow from the first end 210 via the gauze 250 and through the side tube 240 is provided to the bag 100 (not shown in FIG. 3) or directly to ambient; direct venting to ambient is preferred when, for example, screening tests for less dangerous pathogens are being undertaken.

In the collection state, the user 40 places the first end 210 to his/her mouth so that the ring 260 engages and seals onto the user's lips. The user 40 or the tester then activates the assembly 300, for example by depressing an associated foot pump, to eject the jet 310 of saline mist which the user 40 inhales. The inhaled saline mist causes an automatic response in the user 40 to exhale forcefully causing air, mucus and/or sputum droplets in the form of a fine mist to be carried from the user's 40 lungs into the tube 200. A region of the tube 200 around the second end 220 forms a low velocity gas region where exhaled air from the user is inclined to flow in a vortex trajectory and thereby deposit its load of mucus and/or sputum droplets onto internal side-walls of the tube 200. Moreover, the user's 40 exhaled air is vented through the side tube 240 at a relatively high velocity.

A negative partial pressure may additionally be employed to assist in obtaining the sample.

A sample for analysis is thereby provided on the inside surface of the tube 200, especially in the region of the second end 220. The plunger 230 is then actuated relative to the tube 200 for collecting the sample from the inside surface of the tube 200 and then for depositing the collected sample onto an optical interrogation surface of the plunger 230 for subsequent optical interrogation and analysis; such actuation also preferably includes rotation of the plunger 230 relative to the tube 200.

The plunger 230 is thus especially adapted to collecting and mechanically concentrating the sample. Implementations of the plunger 230 will now be described with references to FIGS. 4*a* and 4*b*.

In FIGS. 4*a* and 4*b*, the plunger 230 is substantially cylindrical in form and comprises a central hollow region 400. The plunger 230 is open at its first end and includes a circular flange 410 for abutting onto the second end 220 of the tube 200 when the plunger 230 is fully inserted into the tube 200, thereby limiting an extent to which the plunger 230 can be pushed into the tube 200. The plunger 230 comprises the end surface 270 whose plane is substantially perpendicular to a central longitudinal axis of the plunger 230. At an eccentric region of the surface 270 as shown, there is included an optically transmissive prism 420 extending into the region 400 and a spoon-like projection 430 extending outwardly from the surface 270 remotely from the region 400. The spoon-like projection 430 is susceptible in use to scoop-up mucus and/or sputum from the inside surface of the tube 200 thereonto. The spoon-like projection 430 extends radially at the surface 270 to a peripheral extent of the surface 270. A peripheral edge 440 of the projection 430 is preferably arranged to slidably contact onto the interior surface of the tube 200. An optical aperture 450, also known as a prism window, is included in the end surface 270 so that the prism 420 is in optical communication with sample sputum and/or mucus collected onto the projection 430.

The projection 430 is preferably curved over towards its edge remote from the peripheral edge 440 as shown in FIG. 3*b* to improve performance of the projection 430 to retain thereon sputum and/or mucus collected from the interior surface of the tube 200.

Moreover, the projection 430 is preferably fabricated from a compliant plastics material and arranged to be bendable to squash its load of sample material efficiently across the optical aperture 450 when the plunger 230 is advanced fully into the tube 200 and is resiliently pushed against the aforementioned sealing cap (not shown); suitable plastics materials for the projection 430 include one or more of polyvinylchloride (PVC), nylon, polytetrafluoroethylene (PTFE), polyethylene, polypropylene, alkylene and silicone rubber. If required, the sealing cap can be provided with a recess for accommodating the projection 430 so that a flat non-recessed end surface of the sealing cap adjacent to the recess extends to push and spread a buildup of sample material on a side region of the projection 430 facing towards the optical aperture 450 substantially uniformly onto the aperture 450, thereby providing the system 10 with enhanced detection sensitivity. If required, the thickness of the projection 430 can be reduced to a relative thin neck where it joins onto the end surface 270 to provide a form of hinge so that the projection 430 is tiltable as a flap to squash sample material onto the optical aperture 450.

In order to simplify design of the projection 130 of the reader unit 50, the projection 130 adapted for insertion into the hollow region 400 the plunger 230, it is desirable that the prism 420 is mounted eccentrically but away from the peripheral extent of the surface 270. When the prism 420 and its associated optical aperture 450 are arranged in such a manner, the projection 430 is preferably of a generally "V"-shape form as illustrated in FIG. 4*c*. Such a "V"-shape is especially effective at collecting and retaining a substantial mass of collected sample thereon. Alternatively, as illustrated in FIG. 4*b*, the projection 430 can be of continuously curved form; preferably, the projection 430 at its remote edge is also curved towards the optical aperture 450 nearer towards a central longitudinal axis of the plunger 230.

The plunger 230 is fabricated as a hollow member so that plunger 230 is capable of receiving the projection 130 of the reader unit 50 into the region 400. The projection 130 comprises an electronics module and is preferably of solid cylindrical form as illustrated in FIG. 5 and indicated generally by 500. Whereas, in use, the sample tube 200 and its associated plunger 230 are designed to be disposable items, the reader unit 50 is arranged to be reusable as it comprises moderately costly component parts therein, for example a photomultiplier tube and a diode laser, which will be described in more detail later. The projection 130 is preferably of elongate form comprising a first end 520 and a second end interfacing onto a module including the display 60. The first end 520 comprises an eccentrically-disposed optical interfacing region 510 disposed so as to align with the aperture 450, namely the prism window, when the projection 130 is inserted into the hollow region 400 of the plunger 230 to interrogate a sample collected onto the spoon-like projection 430.

The sample tube 200, the plunger 230 and the projection 130 are of advantage in that they are capable of being compact in storage on account of their mutually concentric mountability. Moreover, the tube 200 in combination with the plunger 230 is capable of collecting and mechanically concentrating substantially the entire sample exhaled by the user 40. Furthermore, the plunger 230 is capable of enabling the reader unit 50 to interrogate the sample without coming into contact with the sample, thereby rendering the reader unit 50 reusable; operational costs are thereby reduced.

The sample tube 200 with its associated side tubes, and the plunger 230 are preferably manufactured from plastics materials, for example one or more of an acrylate, polyethylene, polypropylene, nylon, silicone rubber, polyvinyl chloride (PVC), alkylene, polycarbonate, and polytetrafluoroethylene (PTFE) plastics materials. More preferably, at least one of the tube 200 and the plunger 230 are injection molded. Alternatively, one or more of the sample tube 200 and its associated side tubes, and the plunger 230 can be fabricated from extruded metal sheet, or even fabricated by die-cast metal techniques.

Most preferably, the sample tube 200, the plunger 230 and its associated port 240 and filter 250 are molded as a single component part. Likewise, the plunger 230 with its associated projection 430 and prism 420 are preferably molded as a single component from a substantially optically transparent plastics material, for example a polycarbonate or acrylic plastics material. Alternatively, the plunger 230 can be fabricated from a substantially black plastics material, for example PVC, and the prism 420 subsequently assembled thereinto; the use PVC is of advantage in shielding the prism 420 from stray ambient illumination, and also shielding the remote end of the projection from ambient illumination when inserted into the plunger 230 during measurement.

At the end surface, the plunger 230 can optionally include a small orifice, for example a substantially round orifice having a diameter in a range of 0.1 mm to 2.5 mm. This orifice is of advantage for injecting an atomized spray mist, for example a saline mist, into the sample tube 200 when deployed to collect a sample of mucus and/or sputum from the user 40. Injection of such a mist into the tube 200 prior to the user 40 exhaling the sample for collection onto inner surfaces of the tube 200 is of benefit in obtaining substantial quantities of mucus droplets from the user 40. For other types of bioassay, it is found that the addition of a small quantity of liquid, for example a saline or a buffer solution, is desirable in that it assists the diffusion of microbes, for example bacteria, to be tested towards the optical aperture 450. Such liquids can be added to the system 10 either before or after sample collection, as appropriate using, for example, an aerosol spray or droplets from a pipette.

The tube 200, the plunger 230 and the projection 130 are advantageously fabricated to be within preferred size ranges. For example, the sample tube 200 preferably has a diameter in a range of 20 mm to 30 mm. Moreover, the side tube 240 preferably has a diameter in a range of 1 mm to 10 mm, more preferably in a range of 5 mm to 8 mm. Furthermore, the sample tube 200 preferably has a length in a range of 40 mm to 150 mm, more preferably in a range of 50 mm to 80 mm. The optical aperture 450 preferably has an area in a range of 9 mm$^2$ to 64 mm$^2$. It will be appreciated that these dimensions are appropriate for the system 10 designed for use with human subjects. Other species will require these dimensions to be appropriately modified.

The sample tube 200 and its associated plunger 230 are preferably provided with a locking mechanism such that when the mucus and/or sputum sample has been mechanically concentrated within the tube 200 and delivered efficiently onto the optical aperture 450 and the plunger 230 moved to its measurement position, the plunger 230 is mechanically locked into position relative to the sample tube 200. Such a mechanism is of advantage in that it is capable of preventing the sample tube 200 and its plunger 230 being reused; in poorer parts of the world, there is a temptation to reuse medical parts, for example syringes. More preferably, insertion of the projection 130 of the reader unit 50 triggers engagement of such a mechanism to prevent reuse. A temptation for reuse can potentially occur where the system 10 displays a non-positive indication for the presence of a pathogen. Such a locking mechanism is of further advantage in that locking of the sample tube 200 to the plunger 230 together with the sealing cap forms an enclosed region for isolating dangerous pathogens. Yet more preferably, the sample cap also snap engages onto the tube 200 so that the two cannot subsequently be disengaged.

Figure 6:
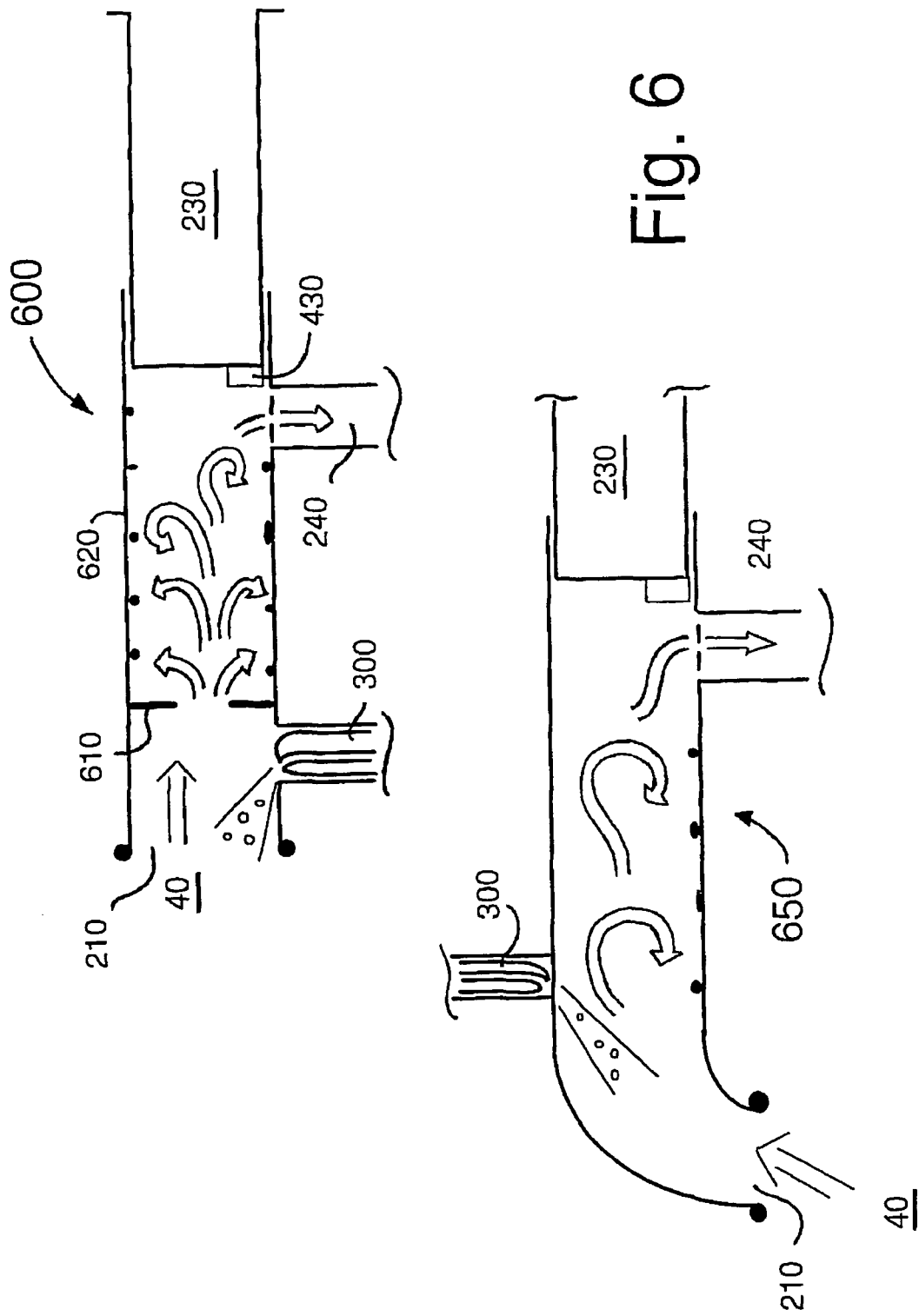
FIG. 6 is an illustration of alternative sample collection tubes for the measurement system of FIG. 1.

In order to enhance a vortex generated within the sample tube 70, 200 and thereby improve sputum and/or mucus deposition therein, the tube 70, 200 can be provided with additional features to modify airflow therein. Referring to FIG. 6, there is shown a modified sample collection tube indicated generally by 600, the tube 600 including an annular septum orifice 610 included between the atomizer assembly 300 and the side tube 240. The septum 610 is preferably included as near as possible to the end 210. Moreover, the septum orifice 610 is preferable molded to be an integral part of a cylindrical part 620 of the tube 600. The projection 430 of the plunger 230 is preferably made flexible so that advancing the plunger 230 into the tube 600 after sample collection therein causes the projection 430 to flex against the septum orifice 610 to squash the sample onto the optical aperture 450.

The septum orifice 610 assists by enhancing peripheral drag to generate eddies and corresponding complex multiple vortex formation, thereby enhancing mucus and/or sputum deposition on an inner surface of the cylindrical part of the tube 600. Moreover, the orifice 60 also assists to prevent saline mist encroaching into regions of the tube 600 remoter from the user 40 in use. Preferably, the septum orifice 610 is recessed behind the end 210 by a distance in the order of 5 mm to 15 mm. Moreover, the septum orifice 610 preferably includes a central hole having a diameter in a range of substantially 3 mm to 20 mm. The septum orifice 610 is preferably fabricated from a collapsible material (for example a flexible plastic) in order that the sample collected on the walls of the sample tube 200, closest to the user's 40 mouth, can be concentrated onto the optical aperture 450.

The sample tube 200 can alternative be modified to include a directional bend near the opening 210 to generate a sample collection tube indicated generally by 650. The assembly 300 is preferably included on an outside bend portion of the tube 650 as illustrated to inject saline mist towards the end 210. The directional bend causes an asymmetrical spatially varying drag to air that promotes eddy formation.

In order to obtain superlative collection performance, a combination of the features of the tubes 600, 650 can be employed.

Further alternative embodiments of sample collection unit 30 are possible.

Figure 7:
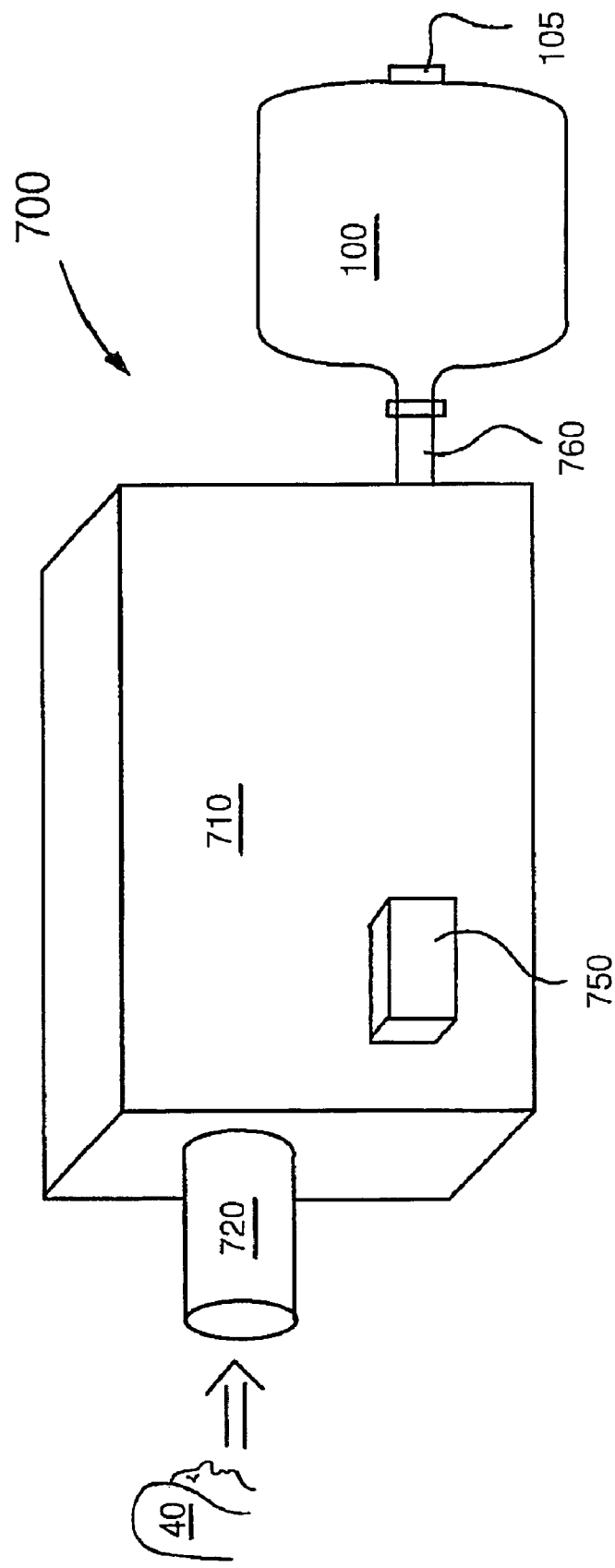
FIG. 7 is a schematic diagram of a yet further alternative sample collection tube for the measurement system of FIG. 1.

For example, in FIG. 7, there is shown a sample collection chamber indicated generally by 700. The chamber 700 comprises an inlet pipe 720 of substantially 25 mm diameter for delivering exhaled breath from the user 40 to a collection box 710. More preferably, the inlet pipe 720 has a diameter in a range of 18 mm to 30 mm. The collection box 710 includes at its periphery a prism 750 susceptible to promoting evanescent radiation propagation at an exposed surface thereof facing inwardly into the box 710 where mucus and/or sputum deposition occurs from the exhaled breath. Sample collection onto the exposed surface is promoted by a vortex generated within the box 710; this vortex is especially enhanced when an exit pipe 760 from the box 710 has a diameter which is less than that of the inlet pipe 720. Preferably, the diameter of the exit pipe 760 is substantially 5 mm, although a diameter in a range of 2 mm to 10 mm is especially preferred. The prism 750 can be situated in any position on the walls of the box 710 in order to collect samples thereon.

Exhaled breath from the box 710 is beneficially conveyed along the exit pipe 760 to the bag 100 and its associated gas exit orifice 105. Alternatively, the exhaled breath output from the box 710 can be initially passed through a filter to remove pathogens and then vented to ambient or to the bag 100. Beneficially, a venturi can be incorporated into the inlet and/or exit pipes to assist with vortex formation within the box 710. The exit pipe 760 and inlet pipe 720 can be placed at any position relative to each other and the prism 750, within the box 710.

Figure 8B:
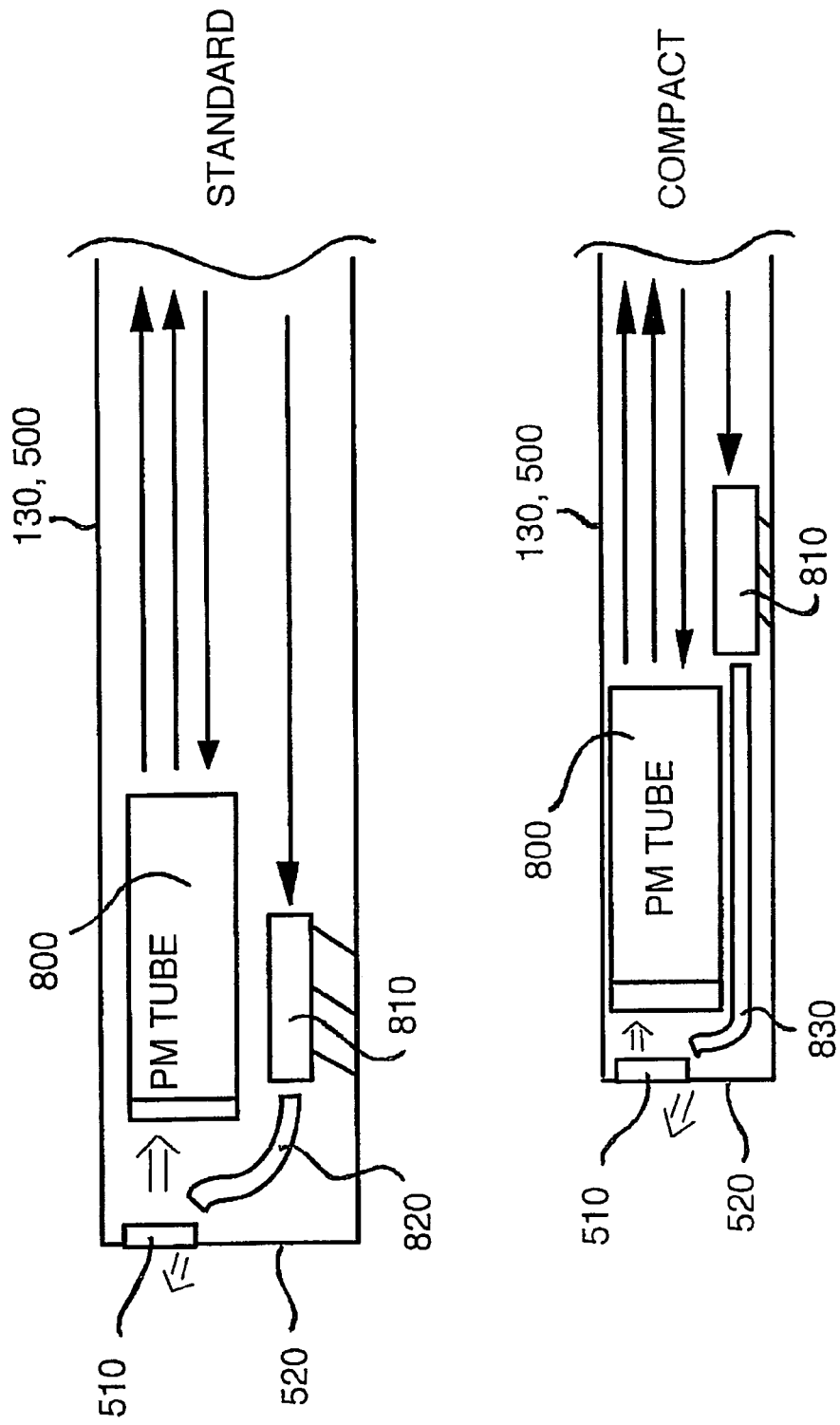

The projection 130 of the reader unit 50 will now be further described in more detail with reference to FIGS. 8a and 8b. In order to obtain optimum readout from the prism 420, optical interrogation components of the reader unit 50 are preferably housed within the assembly. The projection 130 therefore comprises a photomultiplier tube (PM tube) 800 and a diode laser. Advantageously, the PM tube 800 is a proprietary device manufactured by Hamamatsu Photonics K.K. of Japan, the device having a part number R7400U-01. A photosensitive face of the PM tube 800 is orientated towards the optical interface region 510, preferably spatially as close thereto as possible. Moreover, the projection 130 further comprises a solid state diode laser 810. A configuration depicted in FIG. 8a is most preferred as it results in least optical losses when coupling optical radiation to the optical aperture 450. However, especially when the projection 130 is of a relatively small exterior diameter, it is convenient for the diode laser 810 to be coupled via a light guide 820, for example comprising a parallel bundle of optical fibre waveguides. In a standard relatively larger version of the projection 130 illustrated in FIG. 8b, the diode laser 810 and the PM tube 800 are mounted mutually adjacently, thereby requiring only a relatively shorter length of light guide to be employed. However, in a compact relatively smaller version of the projection 130 depicted in FIG. 8b, the diode laser 810 is positioned behind the PM tube 800 as illustrated and a relatively longer section of light pipe 830 employed to convey light from the diode laser 810 to the interface region 510. If required, the projection 130 can be fabricated from diecast, machined or extruded metal and the diode laser 810 can be thermally coupled to the peripheral wall of the projection 130 for cooling purposes. Similar thermal considerations pertain to the PM tube 800 although this device dissipates relatively negligible power in operation. Design of the reader unit 50 comprising the projection 130 and its associated parts will be described in more detail later.

Referring again to FIG. 2, the aforementioned sealing cap applied to the collection tube 70 is denoted by 900. The cap 900 is illustrated in cross-section in more detail in FIG. 9, the cap 900 comprising a main body component 905, first and second liquid reservoirs 910, 920 including liquid masses 930, 940 respectively, and a sealing top 950 hermetically bonded to the body component 905 to seal the liquid masses 930, 940 into the cap 900. The body component 905 and the sealing top 950 are preferably fabricated from a highly flexible plastics material, for example soft silicone rubber. The sealing top 950 is substantially a relative thin flexible membrane including domed regions 960, 970 aligned to corresponding reservoirs 920, 910 respectively. Bonded centrally to the domed regions 960, 970 are steel pins 980, 990 respectively. The steel pins 980, 990 have blunted broadened ends where they are moulded into the sealing top 950, and sharp pointed ends where they face towards end regions of the reservoirs 920, 910. The sealing cap 900 further comprises a retaining feature 1000, for example a barbed insert with backwardly directed barbs, which bind into the collection tube 70, 200 to allow the cap 900 to be easily inserted into the tube 70, 200 but not removed therefrom again.

In operation, the user 40, or preferably the tester, depresses the domed regions 960, 970 to cause the pins 980, 990 to puncture their respective reservoirs 920, 910 to release the contents of their respective liquid masses 940, 930 into the sample tube 70, 200 to chemically process mucus and/or sputum collected at the optical aperture 450 of the plunger 110, 230.

In manufacture, the body component 905 is orientated so that its end face 1010 is downwardly facing. The reservoirs 910, 920 are then filled with their respective liquid masses 930, 940 and then the sealing top 950 comprising its pins 980, 990 is ultrasonically welded, or otherwise hermetically bonded, into a recess molded into the body component 905 as illustrated.

Figure 9:
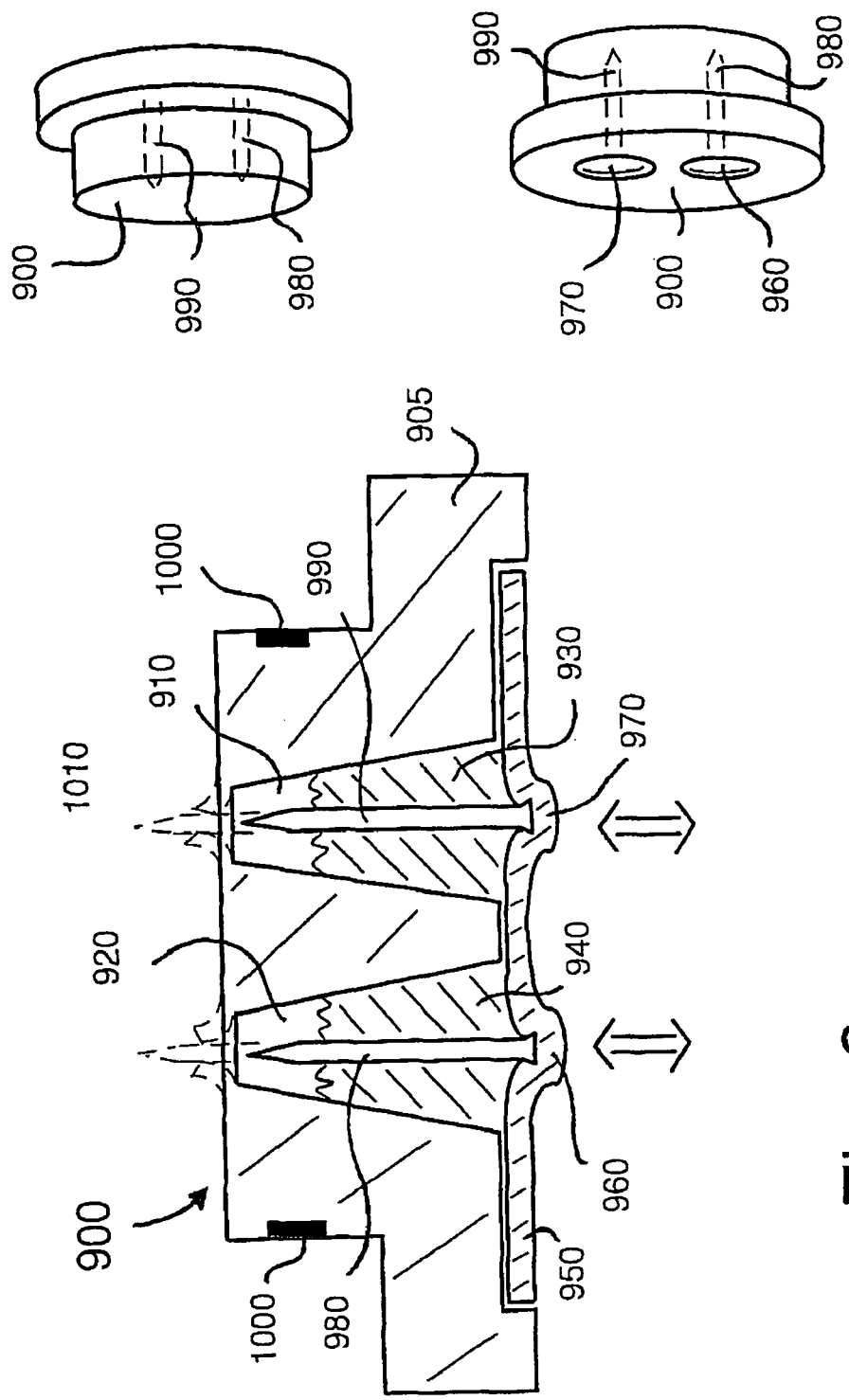
FIG. 9 is a schematic diagram of a sealing cap included within the sample collection unit of FIG. 2.

Although two reservoirs 910, 920 are shown in FIG. 9, it will be appreciated that the sealing cap 900 can be fabricated to have one or more reservoirs. Moreover, the liquid masses 930, 940 can be varied in composition depending upon the type of pathogen to be detected by the system 10. For example, one of the liquid masses can be a biological bacterial lysing agent whereas another of the liquid masses can be a biological fluorescent marker agent. These agents will be described in more detail later.

3.2 Reader Unit

The reader unit 50 illustrated in FIG. 1 will now be described in more detail.

Figure 10:
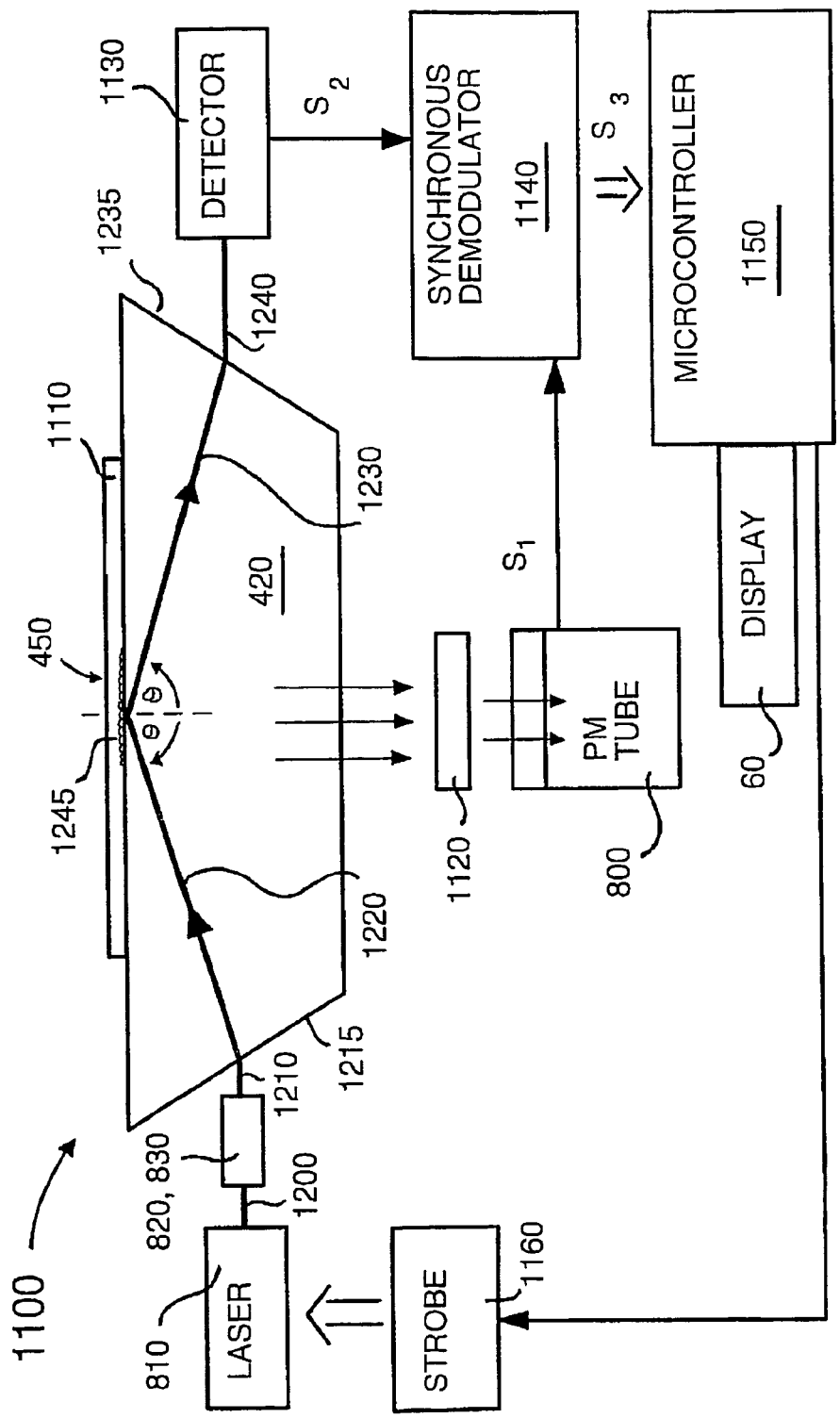
FIG. 10 is a schematic representation of an optical configuration employed within the measurement system of FIG. 1.

Referring to FIG. 10, there is shown an optical configuration indicated generally by 1100. This configuration 1100 is employed in the system 10 and its parts are distributed between the reader unit 50 and its associated projection 130, and the plunger 110, 130.

In particular, the reader unit 50 in its projection 130 includes the laser 810, the light guide 820, 830 (if required), an optical filter 1120, the PM tube 800 (and associated power supply, not shown) and a miniature solid-state diode detector 1130. A main part of the reader unit 50 includes the display 60, a microcontroller 1150 for executing calculations, a synchronous demodulator 1140, and a strobe circuit 1160.

The plunger 110, 230 comprises a prism 420; in particular, the preferred prism 420 is a dove-type prism of a cross-sectional trapezoidal form as illustrated. A major front face of the prism provides the optical aperture 450 that is coated in a biologically active layer 1110 which will be described in further detail later.

Component part interconnection within the configuration will now be described with reference to FIG. 10. The microcontroller 1150 includes a data output, which is coupled to the display 60. In its simplest configuration, the display 60 merely includes a yes/no indicator for indicating whether or not a given pathogen is present in the mucus and/or sputum sample above a predefined threshold. In a more complex configuration, the display 60 provides a quantitative measure of the concentration of pathogens present in the mucus and/or sputum samples being interrogated; the display 60 can be one or more of a liquid crystal display (LCD), for example an alpha-numerical LCD display, a light emitting display (LED) and a miniature plasma display. The microcontroller 1150 is also connected at its output to the strobe circuit 1160 for modulating power applied to the laser 810, thereby temporally modulating its optical output beam 1200 launched into the light guide 820, 830. Moreover, the microcontroller 1150 also includes an input $S_3$ for receiving a demodulated output signal from the synchronous demodulator 1140. The PM tube 800 includes a signal output $S_1$ which is connected to a signal input of the synchronous demodulator 1140. Furthermore, the diode detector 1130 includes a signal output $S_2$ which is coupled to a strobe input of the demodulator 1140. The optical filter 1120 is included between the PM tube 800 and a smaller major rear-plane face 1170 of the prism 420 as illustrated; the filter 1120 is effective at transmitting radiation components arising from evanescent wave interaction in the active layer 1110 and reflecting and/or absorbing scattered radiation generated directly from scatter of primary radiation within the prism 420.

Operation of the optical configuration will now be described with reference to FIGS. 1 and 10. The user 40 activates the system 10 which causes the microcontroller 1150 in combination with the strobe circuit 1160 to generate a modulated signal to drive the diode laser 810 and thereby generate the correspondingly strobed beam 1200. Preferably, the wavelength of radiation output from the laser 810 will be selected to match the excitation wavelength of fluorophores employed to analyse the mucus and/or sputum sample collected onto the optical aperture 450. Such fluorophores can be selected to be selectively responsive at different wavelengths, for example deep red, green, or blue radiation wavelengths. The use of longer wavelength radiation from the laser 810 corresponding to red radiation is preferable to reduce costs, as red lasers are highly inexpensive and readily available. Conversely, solid state laser diodes capable of outputting radiation at relatively shorter blue and green radiation wavelengths are presently relatively expensive. However, a PM tube that is sensitive in the red spectral region must be used and these are slightly more expensive than those most sensitive in the blue/green region. However, the optical configuration 1100 is, therefore, capable of being operated at different wavelengths to match the type of fluorophores employed to analyse the mucus and/or sputum sample, and the system 10 can be constructed to work at any optical frequency desired.

The beam 1200 is preferably strobed at a frequency in a range of 100 Hz to 100 kHz. More preferably, the beam 1200 is strobed at a frequency in a range of 100 Hz to 1500 Hz. Most preferably, the beam 1200 is strobed at a frequency of substantially 1030 Hz as this renders amplifier circuits (not shown) associated with the PM tube 800 and the synchronous demodulator 1140 straightforward to design using standard components as bandwidth constraints are not especially problematic at such a strobe frequency. Moreover, 1030 Hz is not a harmonic of 50 Hz mains supply, thereby rendering the system 10 less susceptible to be affected by 50 Hz fluctuating light sources such as mains-operated fluorescent strip lights frequently found in hospitals and clinics.

Preferably, the strobe circuit 1160 is operable to modulate the injection current used to excite the laser 810 so that this current is periodically switched above and below the lasing current threshold of the laser 810. Alternatively, the laser 810 can be operated at constant output intensity and a separate modulator device, for example a liquid crystal (LCD) cell, used to temporally modulate an output beam from the laser 810 to generate the radiation beam 1200.

The laser 810 emits the strobed beam 1200 which propagates through the light guide 820, 830 to generate a corresponding exit beam 1210 which propagates to a first inclined face 1215 of the prism 420 and is refracted thereat to generate a corresponding refracted beam 1220 which subtends an angle θ relative to a normal to the plane of the optical aperture 450. Preferably, the angle θ is in a range of 62° to 80°. More preferably, the angle θ is substantially 70°.

The refracted beam 1220 propagates to the optical aperture 450 and is mostly reflected thereat to generate a reflected beam 1230 that then propagates to a second inclined face 1235 of the prism 420 to emerge refracted therefrom as a beam 1240, which then propagates to the detector 1130. The beam 1240 gives rise to a strobe signal at the output $S_2$ which is used as a modulation reference signal for the demodulator 1140.

Where the beam 1220 impinges onto the optical aperture 450, a fraction of the radiation present in the beam 1220 is coupled into the plane of the aperture 450 in the form of an evanescent wave 1245. This evanescent wave 1245 propagates in a boundary region at the interface of the biologically active layer 1110 to the prism 420 itself. The boundary region is frequency dependant and at the frequencies in which the system works this is effectively only in the order of 100-200 nm thick. Thus, coupling of the beam 1220 to form the evanescent wave 1245 allows for extremely efficient optical interrogation of chemicals present at the boundary region. If fluorophores are present at the boundary region, they are excited by the evanescent wave to generate fluorescent radiation. Preferably, this fluorescent radiation is at a different radiation frequency to that of the beam so that the filter 1120 can be used to discriminate scattered radiation from the beam 1220 from fluorescence at the aforementioned boundary region; namely, fluorophores present at the boundary region are operable to provide radiation wavelength conversion.

Fluorescent radiation generated at the boundary region propagates from the boundary region through the prism 420 to exit from the prism face 1170 and propagate through the filter 1120 to the PM tube 800 to cause a corresponding sense signal to be generated at the output $S_1$. The sense signal passes to the signal input of the demodulator 1140 and is synchronously demodulated therein with respect to the signal from the output $S_2$ to provide a demodulated signal at the output $S_3$ which passes to the microcontroller 1150 for subsequent sampling and conversion to corresponding data D. The microcontroller 1150 then proceeds to compare the data D with a preprogrammed threshold level T and determine thereby whether or not pathogens are present in the mucus and/or sputum samples collected onto the optical aperture 450 and interrogated by the evanescent wave radiation propagating therealong.

Preferably, the degree fluorescence, namely the magnitude of the data D, can be determined prior to, namely providing data D1, and then again after, namely providing data D2, collecting and mechanically concentrating the sample of sputum and/or mucus onto the optical aperture 450. A difference value given by Equation 1 (Eq. 1):

$$\Delta D = \text{modulus}(D_2 - D_1) \qquad \text{Eq. 1}$$

is then calculated in the microcontroller 1140. This difference value ΔD is then compared with the threshold value T to determine whether or not pathogens are present in the sample. Such a difference method of measurement is effective at removing systematic contributions to the sense signal provided at the output $S_1$; such systematic contributions can arise from scatter within the prism 420, residual fluorescence within the prism 420 especially if it is fabricated from plastics materials, and finite radiation wavelength discrimination provided by the filter 1120. Suitable plastics materials for fabricating the prism 420 include perspex, acrylate, polycarbonate and polymethylmethacrylate (PMMA). It should be noted that the use of polymer materials that exhibit fluorescence is be avoided where possible.

Preferably the threshold value T is made proportional to the optical interrogation radiation power delivered into the beam 1210 from the laser 810. More preferably, the threshold value T is made proportional to the radiation power in the beam 1240 received at the detector 1130 so as to account for efficiency of optical coupling into the prism 420 which can potentially vary from plunger 230 to plunger 230, especially if mechanical tolerances in manufacture are not tightly controlled.

Although the use of the PM tube 800 is described in the foregoing, it will be appreciated that other types of optical detectors can potentially be employed, for example avalanche photodiodes, phototransistors or low-noise photodiodes. If signal-to-noise considerations allow, the laser 810 is preferably substituted with a lower-cost high-brightness light emitting diode (LED).

If required, the filter 1120 can comprise several optical filter components to enhance its wavelength discrimination, for example by utilizing several diffraction grating layers. Moreover, the microcomputer 1150 can be programmed to account for systematic steady temporal drift in the sense signal to account for warm-up characteristics of the system 10 when activated from a cold state. An estimate of such drift can be made by interrogating the optical aperture 450 for a period of a few minutes before introducing the mechanically concentrated sample thereto.

Preferably, the microcontroller 1150 includes a data logger for recording test results and corresponding reference codes for subsequent downloading to a database from the reader unit 50. In such a configuration, the reader unit 50 preferably includes a data entry keypad so that each test performed by the reader unit 50 can be allocated an identification reference. When the microcontroller 1150 is configured to provide a data-logging characteristic, the microcontroller 1150 can potentially be used effectively during a disease epidemic to generate pathogen infection rate statistics.

Figure 11:
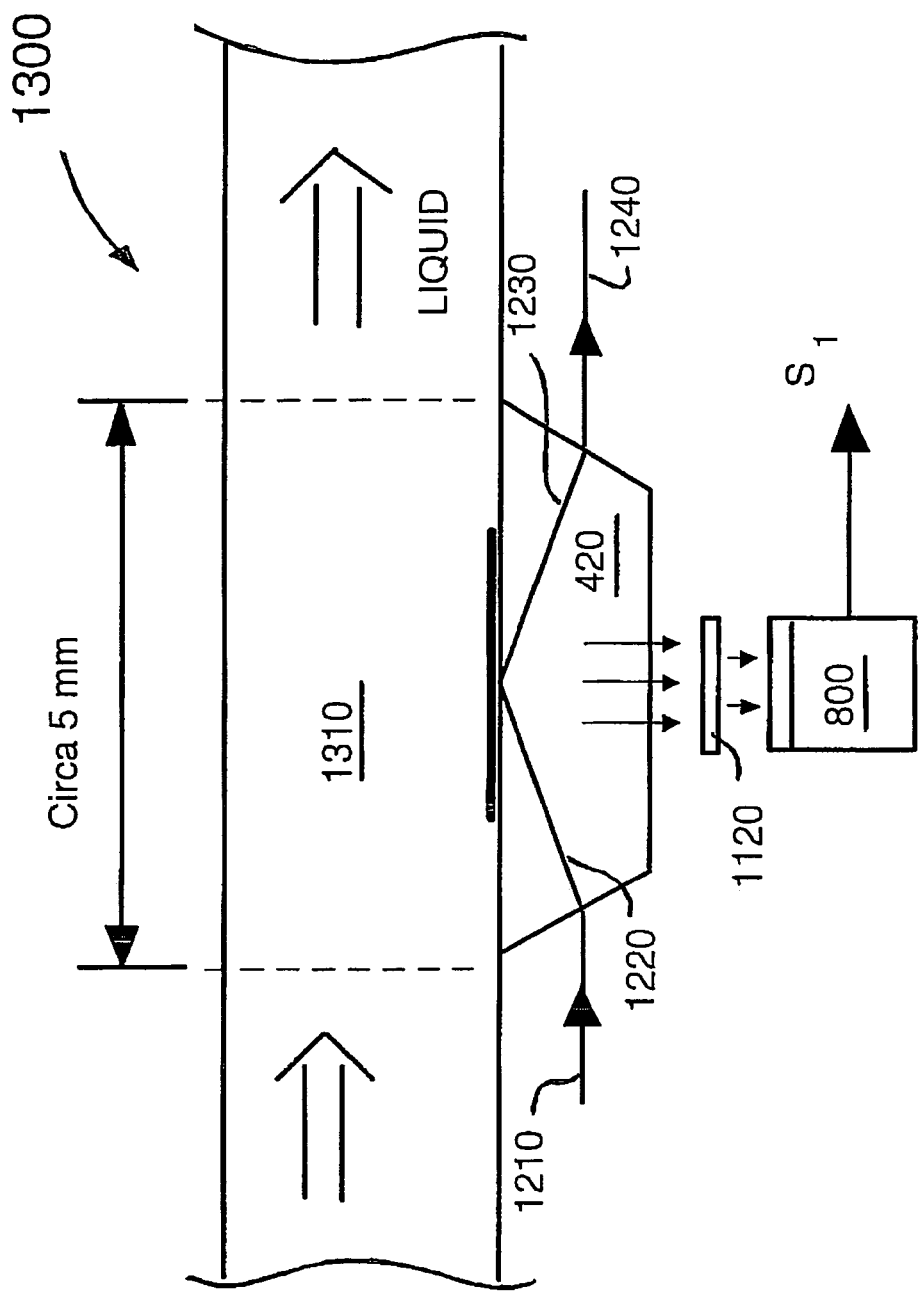
FIG. 11 is an illustration of a modification to the measurement system of FIG. 1 for the analysis of liquid samples such as blood.

It will be appreciated that the system 10 can be adapted for interrogating liquid samples from other sources than exhaled breath. Referring to FIG. 11, there is shown a alternative configuration for part of the system 10 for analysing a liquid, for example a blood sample, flowing or stagnant within a tube 1310. The prism 420 is an integral part of, or is attached to, a side region of the tube 1310. The beam 1210 passes through the prism 420 as the beams 1220, 1230 and excites fluorophores attached to the major face of the prism 420 facing in contact towards the liquid sample within the tube 1310. Fluorescence of the fluorophores in response to composition of liquid sample, for example blood, is received by the PM tube 800 to generate a strobe sense signal at the output $S_1$ for subsequent synchronous detection. The system 10 modified according to FIG. 11 is thus susceptible to provide continuous monitoring of blood or other body fluids, for example urine, for pathogens and therefore has widespread potential application in hospitals and body fluid processing facilities.

Moreover, if required, a sample air stream can be continuously passed through the tube 1310 to detect for air-borne pathogens, toxic pollutants and explosive vapors for example. Thus, the biological measurement system 10 is potentially adaptable to other applications other than merely to detect respiratory pathogens such as tuberculosis.

Figure 12:
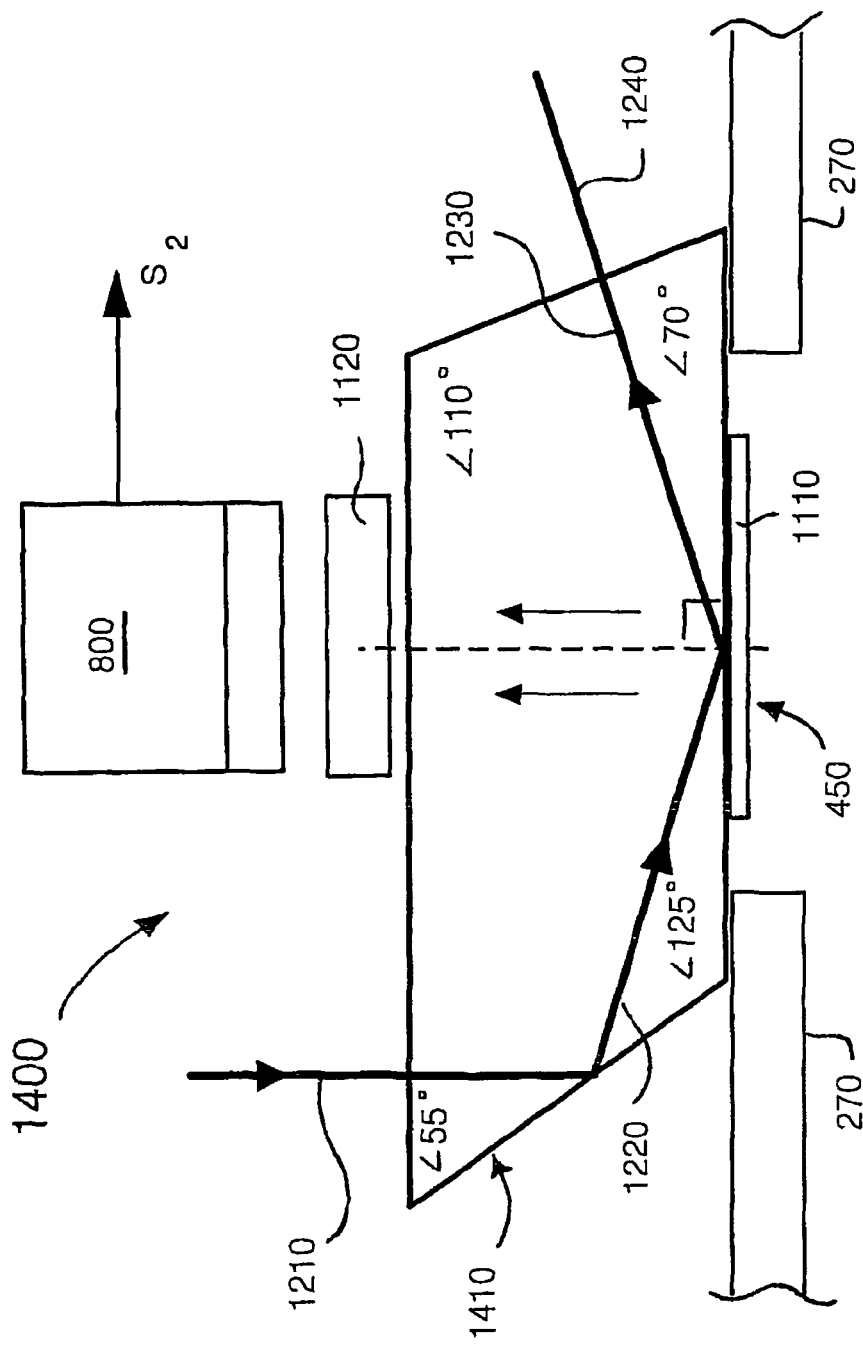
FIG. 12 is a schematic diagram of a compact dove prism for incorporation into the measurement system of FIG. 1.

The dove-type prism 420 can be substituted in the plunger 110, 230 with an alternative prism indicated generally by 1400 in FIG. 12. The prism 1400 preferably has internal angles of 55°, 125°, 70° and 110° as illustrated. Optionally, a face indicated by 1410 can be a mirror coated surface to enhance reflective performance of the face 1410 when reflecting the beam 1210 to form the beam 1220. By reducing internal reflection losses, the prism 1400 is potentially capable of imparting an enhanced detection signal-to-noise ratio to the system 10.

Furthermore, dove-type or other prisms where the angle of acceptance is such that multiple reflections are induced within the prism can be adopted. For example, suitable alternative prisms are described in a book by C. N. Banwell and E. M. McCash, "Fundamentals of Molecular Spectroscopy" (1994) McGraw-Hill, $4^{th}$ edition which is herewith incorporated by reference.

It should be appreciated that fluorimetry has been shown to be of considerable importance for the detection of biological materials such as proteins and DNA, where fluorophores on antibodies are used as markers for detection. Detection using such fluorimetry can be executed by way of either:

(a) bulk fluorescence measurements; or
(b) through the application of interrogation techniques such as evanescent wave detection; or
(c) cavity ring down spectroscopy; or
(d) through the use of displacement assays.

Such fluorimetry offers some potential advantages in terms of specificity, simplicity, and sensitive. Evanescent wave detection is well known, but low-cost evanescent wave fluorimeters are not yet commercially available for use in pathogen detection as described with respect to the present invention.

It should be further appreciated that sample analysis following collection onto an optical interrogation area can be undertaken using means other than fluorimetry, for example, radioactive and phosphorescent markers can be utilized or chemiluminescence techniques.

Detection can also be carried out using other forms of spectroscopy, not associated with immunoassay systems or evanescent waves. For example, infrared spectroscopic methods can identify the presence of specific molecular fragments on the basis of 'group frequencies' at specific regions of the infrared spectrum; these can be performed using both transmission and reflection geometries where the latter detects the absorption of evanescent IR radiation. Other possibilities are preferably, but not exclusively, Surface Acoustic Wave (SAW) detection and Surface Plasmon Resonance (SPR) which may provide signal enhancement and thus gains in sensitivity.

4. System Biochemistry

In the foregoing, the measurement system 10 is described with respect to its hardware. In the following description, chemical aspects of the system 10 will now be elucidated in more detail.

4.1 Biochemical Overview

The measurement system 10 is capable of operating according to two alternative detection methods, namely either:

(a) by fluorophore displacement resulting from the presence of a pathogen (namely competitive displacement assay); or
(b) by fluorophore binding promoted by the presence of a pathogen (namely selective binding assay).

In the competitive displacement assay, the sense signal at the output $S_1$ reduces as the pathogen is introduced into the sample collection unit 30. Conversely, in the selective binding assay, the sense signal at the output $S_1$ increases as the pathogen is introduced into the collection unit 30. Both assays are pertinent as certain types of pathogen are best detected by one or other of the assays.

In the selective binding assay, the optical aperture 450 is coated during manufacture with a first antibody that will bind to the pathogen to be detected. In operation, the pathogen is mechanically concentrated onto the optical aperture 450 and becomes immobilized thereat on account of its affinity to the first antibody. Next, fluorophores bound to second antibodies having affinity to the pathogen are released into the sample tube 70, 200 so that the fluorophores become bound to the pathogen immobilized to the first antibodies at the optical aperture 450. If required, the first and second antibodies can be identical although this is not essential as pathogens frequently exhibit several surface regions to which different antibodies can bind. The second antibodies and their associated fluorophores can be in the form of a liquid held in one of the reservoirs 910, 920 of the sealing cap 900. When the pathogen has been immobilized directly to the first antibodies at the optical aperture 450 together with the fluorophores bound to the second antibodies immobilized to the pathogen, the evanescent wave radiation 1245 is capable of interacting strongly with the fluorophores, thereby generating significant fluorescence for detection by the PM tube 800.

In the competitive binding assay, the optical aperture 450 is coated during manufacture with the first antibody that will bind the pathogen being investigated. Moreover, during manufacture, fluorophores bound to analogues of the pathogen that bind weakly to the first antibody are added to the optical aperture 450. When the mechanically concentrated sample is applied to the aperture 450, the pathogen therein displaces the weakly bound fluorophores and associated analogues and bind in substitution to the immobilized first antibodies. The weakly bound fluorophores and associated analogues, when displaced, migrate away from the boundary region supporting the evanescent wave propagation 1245 causing a decrease in fluorescence detected by the PM tube 800. Preferably, one or more of the reservoirs 910, 920 of the sealing cap 900 includes a wash agent to assist removal of the displaced fluorophores bound to associated analogues from the optical aperture 450 so that a final settled reading is more rapidly attained.

It should be noted that the antibodies that can be used for these tests may be monoclonal or polyclonal in form.

4.2 Antibody Immobilisation

The immobilisation of antibodies to glass or plastic surface, for example to the optical aperture 450, is already well studied, and many protocols exist. These protocols derive largely from the success of known ELISA tests, in which antibodies immobilised on a 96-well plate form a crucial component of such tests. In a textbook "Immobilized Biomolecules in Analysis: a practical approach", edited by T. Cass and F. S. Ligler (Oxford University Press), said textbook herewith incorporated by reference, there is provided a thorough overview of many immobilisation protocols.

Such protocols will each typically comprise:
(a) a preparation step, in which a surface is cleaned and optionally activated;
(b) an incubation step during which antibodies or antibody fragments are attached to the surface; and then
(c) a blocking step to prevent further non-specific binding of biomolecules to the surface Rinsing steps generally follow the incubation and blocking steps. The prepared surface is then dried and stored in a dry atmosphere. Incubation times depend to a significant extent on the molecule (namely pathogen) to be captured and the surface composition.

Activation of the surface is commonly achieved by irradiating the surface, or exposing it to plasmas or chemicals such as silanes incorporating an active group to which antibodies can be bound. Once chemically active groups exist on the surface, a simple incubation step is usually sufficient to bind the antibodies, such antibodies also referred to in the following as receptors.

4.3 Analogues for the Competitive Binding Assay

Analogues used in the aforementioned competitive displacement assay correspond to molecules or molecular groups which bind to receptors, for example antibodies, immobilised on the optical aperture 450 of the prism 420, but do so with a lower association constant than the pathogen to be detected. Preferably, the analogue-receptor association constant is less than 10% of the pathogen-receptor association constant, and if possible less than 1%.

These analogues may be similar molecules from closely related species, for example sheep luteinising hormone is capable of providing an analogue of human chorionic gonadotropin. Alternatively, the analogues can be molecules synthesised to mimic the structure of the pathogen, especially the epitope to which the antibody binds, or a modified version of the pathogen.

It is also potentially advantageous to use derivatives of the pathogen as analogues. Such derivatives can be artificial derivatives such as molecules modified by adding bulky or ionic groups (which can reduce the binding energy), by adding steric or charge interference, or binding to a bulky group, which can cause a conformational change in the binding site of the pathogen. In the case of analytes which are proteins, the corresponding amino acid sequence of the protein can be modified near the binding site to the receptor by recombinant molecular biology techniques, such as site directed mutagenesis. Alternatively they can be natural metabolites of the target analyte.

Techniques required to prepare such analogues are known, and there is much prior art on the design of such analogues. Chemical modifications of organic molecules, biochemical modifications of naturally occurring molecules and synthesising structural mimics or molecules are known in the art. The suitability of a candidate analogue can be determined by a competitive ELISA assay between the analyte and the candidate analogue or by a measurement of the association constant with the receptor.

Polyclonal and monoclonal antibodies reactive against pathogens such as *mycobacterium tuberculosis* are readily available from several commercial vendors, for example Skybio Ltd. in the United Kingdom. Such antibodies can be purchased in sizeable batches and labeled and immobilized using standard known chemistries.

4.4 Fluorophores

Selection of suitable fluorophores for use in the system 10 has an important bearing on the technical performance of the system 10, for example its signal-to-noise ratio and hence its ability to identify early onset of disease.

There are many commercially available fluorophores. The most significant qualities of such fluorophores are:
(a) their absorption band, which limits the range of interrogating radiation wavelengths at which they can be excited; and
(b) their emission band, namely the range of wavelengths over which fluorescent radiation is emitted from the fluorophores when excited.

The absorption band must overlap as much as possible with the spectrum of the interrogating light source used, namely the laser 810 in the system 10; moreover, the emission band should overlap as little as possible with the absorption band. These qualities limit the range of fluorophores, which can be used in the system 10. Other factors, which may influence the choice of an optimal fluorophore for the system 10, are:
(a) the ease with which the fluorophore can be coupled to a corresponding target molecule, for example an antibody or analogue; and
(b) the separation between the absorption and emission bands of the fluorophore; and
(c) the brightness of the fluorescent radiation emitted from the fluorophore.

A commercial company Molecular Probes manufactures and supplies a commercial range of fluorescent dyes called the Alexa dye series. This series includes a number of bright fluorophores with optimal excitation wavelengths ranging from 346 nm to 684 nm, including many molecules specifically designed to work well with common light sources such as bright laser diodes or red LEDs. Many other dyes exist and are widely used, for example fluorescein isothiocyanate (FITC), BODIPY, phycoerythrin, allophycocyanin (APC), rhodamine, Texas Red and Oregon Green. Some of these dyes and their relevant parameters are listed in Table 1; one or more these dyes can, if required, be employed in the system 10 either alone or in combination.

TABLE 1

Examples of typical fluorophores susceptible for use in the system 10.

| Dye name | Abbreviation | Absorption peak (nm) | Emission peak (nm) |
|---|---|---|---|
| Fluorescein isothiocyanate | FITC | 493 | 520 |
| R-phycoerythrin | RPE | 495, 536 | 576 |
| B-phycoerythrin | BPE | 546 | 576 |
| Rhodamine | — | 550 | 573 |
| Rhodamine B | — | 578 | 604 |
| Allophycocyanin | APC | 630, 645 | 655, 660 |
| Alexa Fluor 350 | — | 346 | 442 |
| Alexa Fluor 430 | — | 433 | 539 |
| Alexa Fluor 488 | — | 495 | 519 |
| Alexa Fluor 532 | — | 532 | 554 |
| Alexa Fluor 594 | — | 590 | 617 |
| Alexa Fluor 633 | — | 632 | 647 |
| Alexa Fluor 680 | — | 684 | 707 |
| BODIPY 493/503 | — | 500 | 506 |
| BODIPY 665/676 | — | 665 | 676 |
| Cy5 | — | 649 | 666, 670 |
| Texas Red | — | 595 | 620 |
| Teramethyl rhodamine isothiocyanate | TRITC | 550 | 573 |

In order to enhance performance, latex spheres, fluorescent materials can be bound to one or more of antibodies and analogues in order to provide the system 10 with enhanced detection sensitivity. Such latex spheres are capable of exhibiting an enhanced degree of fluorescent radiation in response to being excited by the evanescent radiation wave 1245 at the optical aperture 450.

Latex spheres are commercially available from companies such as Dynal Biotech with a wide range of surface chemistries; such surface chemistries can include fluorophores and also impart the spheres with magnetic properties. In the sample tube 70, 200, magnetic attraction of latex spheres comprising fluorophores when mechanically concentrating the sputum and/or mucus sample onto the projection 430 is highly advantageous to achieving enhanced measurement sensitivity from the system 10. The latex spheres used for this system are preferably in the range of 50 nm to 1 µm in diameter; more preferably, the spheres are in the range of 100 nm to 200 nm in diameter, namely in line with the boundary depth of the evanescent wave penetration at the optical aperture 450.

In the selective binding assay, magnetically labeled fluorescent latex spheres can be released from one of the reservoirs 910, 920 of the sealing cap 900 into the sample tube 70, 200 prior to mechanical concentration of the sample at the optical aperture 450; preferably, the aperture 450 and/or the projection 430 are provided with one or more, small, movable, permanent magnet(s) thereat to assist latex sphere collection. Following collection and concentration of the sample onto the optical aperture 450, the magnet(s) can be moved away to allow the spheres that have not been chemically bound to the aperture 450 to diffuse away into the bulk liquid, leaving only the bound species to be detected at the aperture 450.

4.5 Optional Lysis Sensitivity Enhancement

Sensitivity of the system 10 to the detection of pathogens can be enhanced by employing a process known as lysis. Lysis is the process of breaking cells, for example pathogen microbes, into its component fragments. Antibody-labeled fluorophores are capable of binding to these fragments. Moreover, the fragments are susceptible to binding to antibodies at the optical aperture 450.

There are a wide variety of methods used to lyse microbes, for example bacteria. Such methods comprise one or more of chemical, mechanical and thermal processes. These processes are known to the skilled addressee. Lysis of pathogens collected within the sample tube 70, 200 is of advantage in that lysis fragments are susceptible to binding to first antibodies immobilized at the optical aperture 450 and also to second antibodies bound to associated fluorophores. Thus, lysis is capable of enhancing the detection efficiency in the aforesaid selective binding assay within the system 10, for example by at least an order of magnitude. Likewise, lysis is capable of giving rise to more competitive displacement sites at the optical aperture 450 in the case of the aforesaid competitive displacement assay.

Chemical methods of lysis involve the use of enzymes such as lysozyme, or detergents such as SDS to break down cell walls. Mechanical methods physically break down cell membranes; examples of mechanical methods include nitrogen cavitation bombs, french press or hughes press, sonication, glass beads or osmotic lysis techniques. Thermal lysis employs extremes of temperature excursions to destroy cell walls; such temperature excursions can comprise repeated freezing and thawing of a cell culture.

*Mycobacteria*, for example *mycobacterium tuberculosis*, are especially difficult to lyse. Lysis buffers specifically adapted for mycobacteria comprise additional reagents such as lysozyme to break down mycobacteria cell walls.

During lysis, enzymes released from cell interior regions often attack molecules of interest for detection purposes within the system 10. However, lysis buffers can be formulated to include additional ingredients such as protease inhibitors to prevent the target molecule from being digested or denatured. Table 2 provides a list of lysis protocols susceptible for use within the system 10 to enhance its pathogen detection performance.

TABLE 2

Examples of lysis protocols

| Reference | Method | Principles used | Class of target |
|---|---|---|---|
| Gen-Probe package insert | Sonicate for 15 minutes in lysis buffer and glass beads | Mechanical, chemical | Mycobacterium |
| Pierre et al., J. Clin. Micro. 29 (4): 712-717 (1991) | 15 minutes at 95° C. with 0.1M NaOH, 2M NaCl, 0.5% SDS | Thermal, chemical | Mycobacterium |
| Hurley et al, Int. J. Systematic Bacteriology 38 (2): 143-146 (1988) | 3 minutes in minibead beater with distilled phenol and zirconium beads | Mechanical | Mycobacterium |

TABLE 2-continued

Examples of lysis protocols

| Reference | Method | Principles used | Class of target |
|---|---|---|---|
| Robson et al., U.S. Pat. No. 5,376,527 | Heating for 2 to 15 minutes at 60° C. to 100° C. | Thermal | Mycobacterium |
| Pierce product information | Shake sample with B-PER Bacterial Protein Extraction Reagent for 10 minutes | Chemical | Bacterium |

Lysis is preferably performed in the collection apparatus 30 either before mechanical concentration of the sample has occurred therein or after mechanical concentration has been achieved.

It will be appreciated that sensitivity of the system 10 can be further enhanced by utilizing many known amplification techniques employed in standard immunoassay. Such amplification techniques include, but are not limited to, biotin/axidine or Biotin/streptavidin sandwich techniques and enzyme-linked assays. Also, chromogenic substances can be used in substitution, or in addition to, the fluorophores, for example as in ELISA assays, producing a colour change in solution rather than fluorescent signal as in the system 10 described above. Such colour change can be detected electronically using colour sensitive electronic detectors or using the naked eye.

4.6 Description of Biochemical Interactions within the System

In order to more completely describe operation of the system 10, especially with regard to biochemical reactions occurring therein, reference will be made to FIGS. 13 to 15.

4.6.1 Selective Binding Assay

Figure 13:
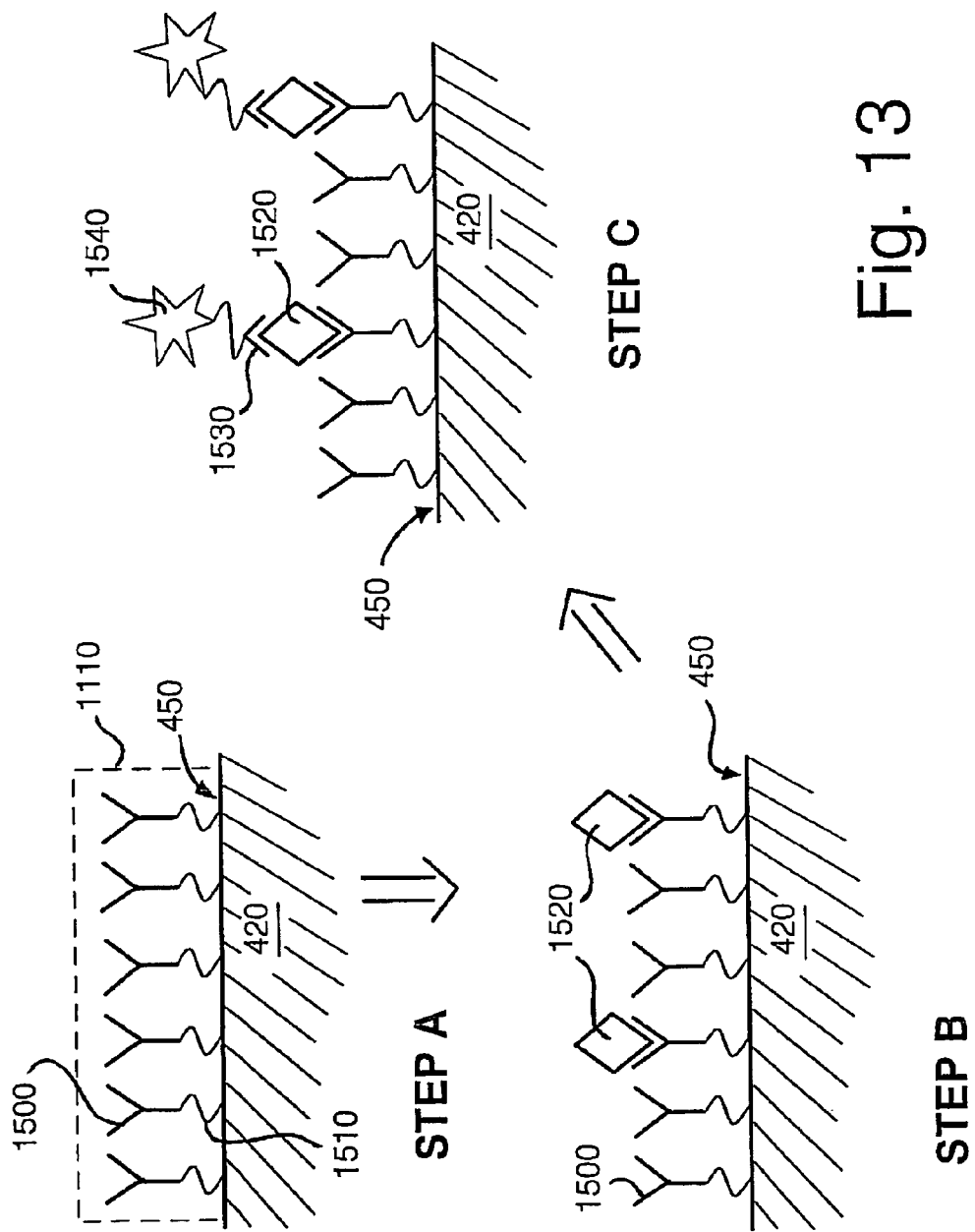
FIGS. 13 and 14 are depictions of a selective binding assay employed in the system of FIG. 1.

Referring to FIG. 13, there is illustrated a binding process which occurs in operation within the sample tube 200 at the optical aperture 450.

In STEP A, the first antibodies denoted by 1500 are bound to the optical aperture surface 450, the first antibodies 1500 deposited during fabrication of the plunger 110, 230. The optical surface is optically interrogated with evanescent wave radiation and a first degree of fluorescence measured.

In STEP B, the mucus and/or sputum sample is mechanically concentrated within the sample tube 70, 200 as described in the foregoing and deposited at the optical aperture 450 whereat specific pathogens 1520 of interest bind to the first antibodies 1500 as illustrated.

In STEP C, the fluorophore-labeled second antibodies 1530, 1540 are released from one or more of the reservoirs 910, 920 of the sealing cap 900 by rupturing them as described earlier with reference to FIG. 9; the fluorophore-labeled antibodies 1530, 1540 wash onto the optical surface 450 as in STEP B and bind to the specific pathogens 1520 in STEP C. The optical aperture 450 with its bound first and second antibodies, 1500, 1530, pathogen 1520 and fluorophores 1540 can then be optically interrogated using evanescent wave radiation of identical magnitude as used to determine the first degree of fluorescence, thereby enabling a second degree of fluorescence to be measured. A difference between the first and second degree of fluorescence gives an indication of the presence of the fluorophores 1540 from which can be inferred the presence of the pathogen 1520.

Figure 14:
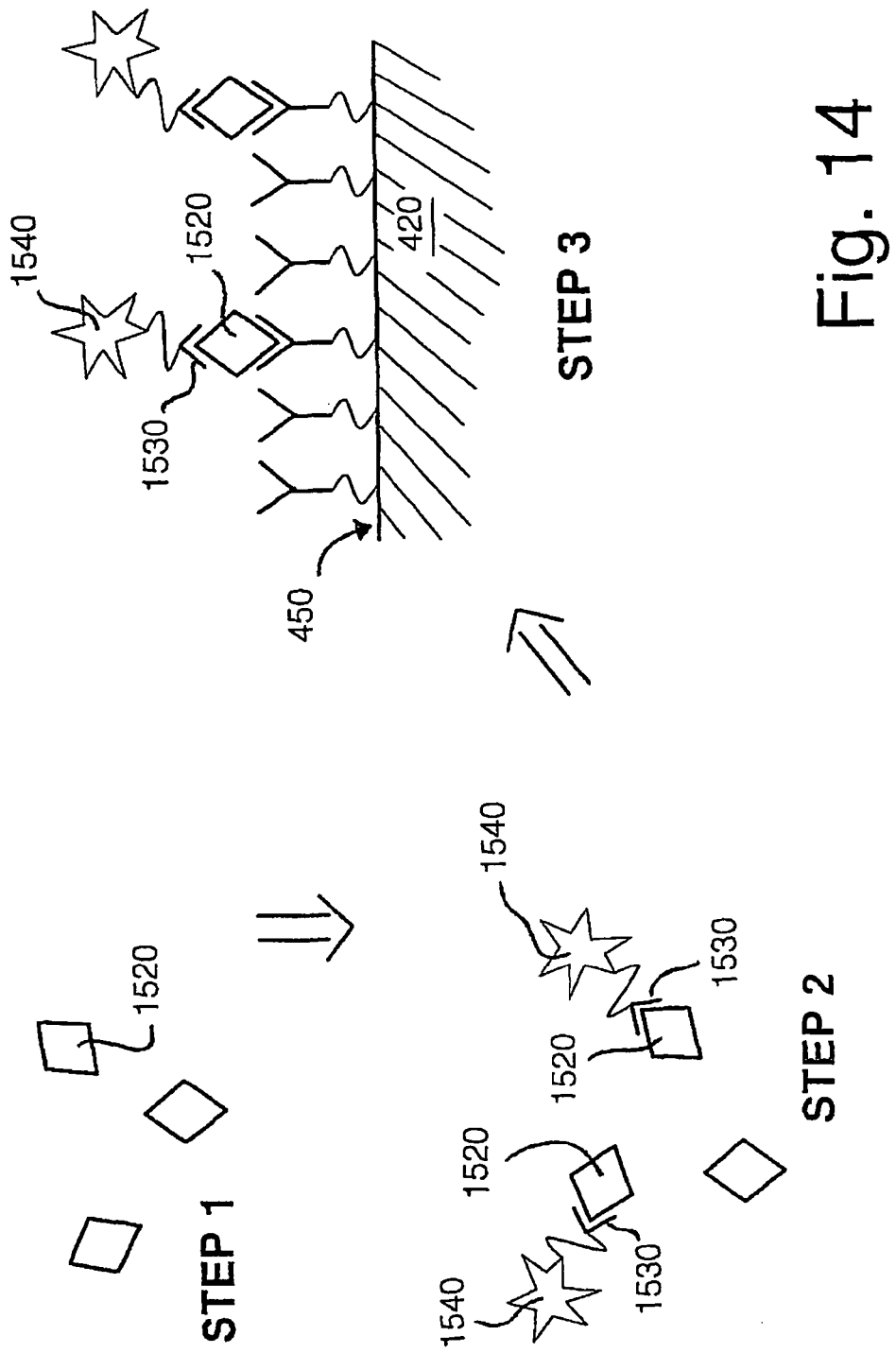

A variation on the process of FIG. 13 is possible as depicted in FIG. 14.

In STEP 1 of FIG. 14, the pathogen 1520 in the form of mucus and/or sputum is deposited onto inside walls of the sample tube 70, 200.

In STEP 2, the second antibodies 1530 and their associated fluorophores 1540 in the form of latex spheres are then released from one or more of the reservoirs 910, 920 in the sealing cap 900. The second antibodies 1530 bind to the pathogen 1520 within the sample tube 200. The plunger 230 is then used to mechanically concentrate the pathogens 1520 bound to their second antibodies 1530 and associated relatively large latex spheres. Such an order of steps means that there is a relatively large fluid mass to collect than in FIG. 13; this relatively larger mass is of benefit where relatively little mucus and/or sputum is deposited within the tube 200.

In STEP 3, the pathogens 1520 bound to the second antibodies 1530 and their latex sphere laden fluorophores 1540 are then presented to the optical aperture 450 whereat they bind to the first antibodies 1500 immobilized onto the aperture 450. The pathogens 1520, the antibodies 1500, 1530 and the fluorophore-laden latex spheres thereby become bound to the aperture 450 and fluorescence when interrogated with evanescent radiation to signal presence of the pathogen 1520 in the sample.

4.6.2 Competitive Binding Assay

Figure 15:
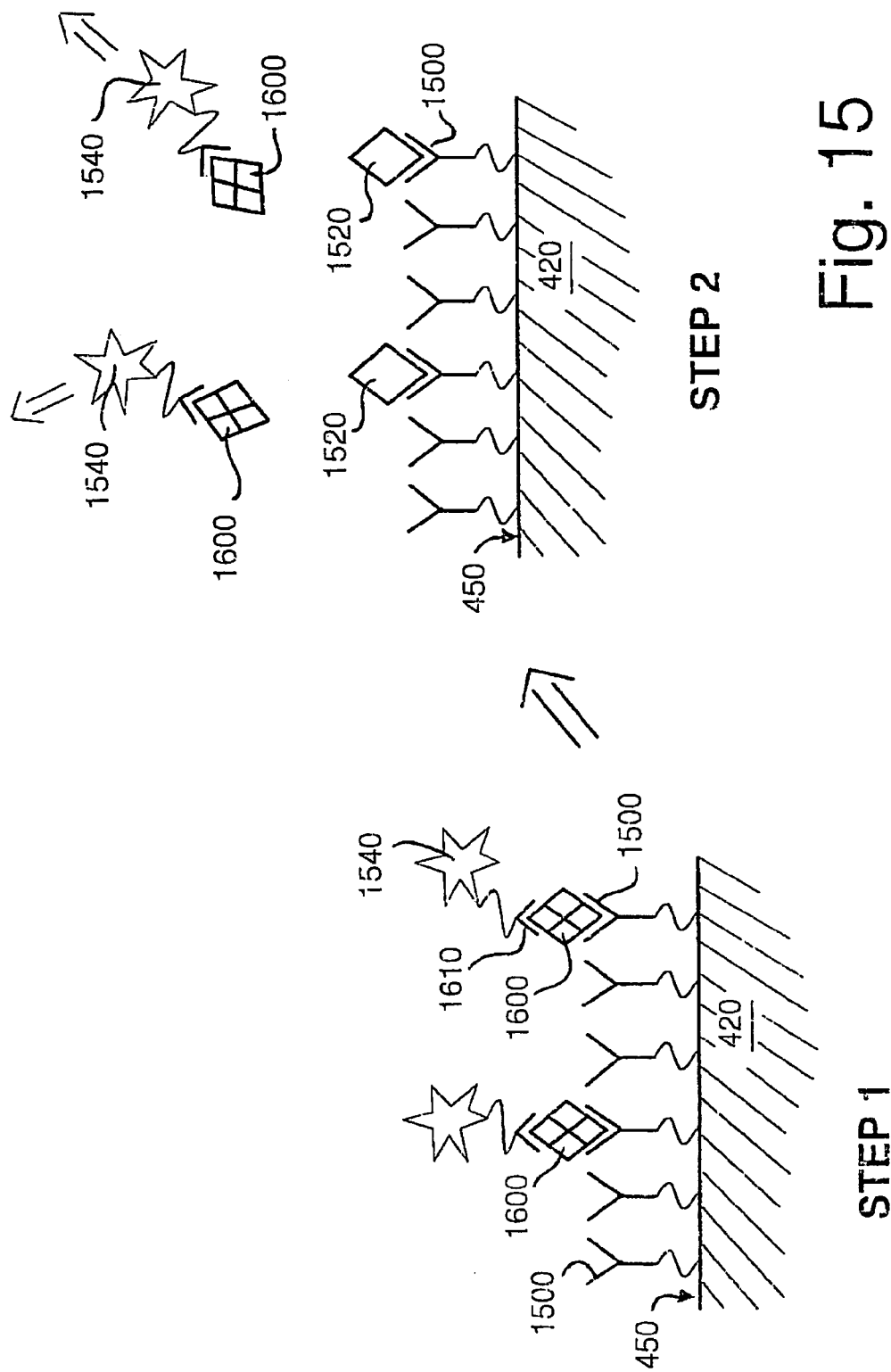
FIG. 15 is a depiction of a competitive displacement assay employed in the system of FIG. 1.

The competitive binding assay is depicted in FIG. 15.

In STEP 1, the optical aperture 450 has bound thereto during fabrication the first antibodies 1500. Moreover, analogues 1600 of the pathogen 1520 to be detected are added to the aperture 450 for weakly binding to the immobilized first antibodies 1500. The analogues 1600 have tightly associated thereto third antibodies 1610 bound to the fluorophores 1540; the fluorophores 1540 can, if required, be fluorophores bound in the aforesaid latex spheres.

In operation, the optical aperture 450 is interrogated using evanescent radiation to obtain a first fluorescence measurement. Next, a mucus and/or sputum sample is collected in the interior surface of the tube 200. The sample is then mechanically concentrated using the plunger 230 as described in the foregoing and finally deposited onto the optical aperture 450.

In STEP 2, the pathogens 1520 in the mechanically-concentrated sample have greater affinity for the first antibodies 1500 and competitively displace the analogues 1600 which become detached and migrate with their associated fluorophores to regions remote from where the evanescent radiation propagates at the optical aperture 450. The optical aperture 450 is then interrogated for a second time with evanescent wave radiation of identical amplitude to that use to obtain the first measurement; a second fluorescence measurement is thereby obtained. A difference between the first and second measurements is indicative of the number of displaced fluorophores and hence, by inference, the presence of the pathogen 1520 in the collected sample.

4.6.3 Assay Detection Methods not Involving Fluorescence or Evanescent Waves

The measurement system 10 can be adapted to utilize a detection and labeling scheme that does not rely on evanescent wave excitation of fluorescence. An example of such a scheme will be outlined:

Standard Method:

| STEP 1: | Incubate sample with surface-bound IgG; any analyte present is immobilised at surface by IgG |
|---|---|
| STEP 2: | Rinse |
| STEP 3: | Incubate with labeled IgG. If any immobilised analyte is present, labeled IgG is immobilised at surface |
| STEP 4: | Rinse to remove unbound IgG and label |
| STEP 5: | Add developing agent if required |
| STEP 6: | Measure result |

With all such schemes, if monoclonal antibodies targeted at two different epitopes are used, it is potentially possible to perform the two incubation steps simultaneously, thereby circumventing the need to rinse between the at STEPS 2 and 4.

Possible labels include, but are not limited to, substances listed in Table 3.

TABLE 3

Chemical labels

| Technique | Label | Developing agent | Measurement |
|---|---|---|---|
| Chromogenic ELISA | chromogenic enzyme | Enzyme substrate | Bulk colourimetry |
| Fluorogenic ELISA | fluorogenic enzyme | Enzyme substrate | Bulk fluorescence |
| Chemiluminescent assay | chemiluminescent molecule | Chemiluminescent substrate | Chemiluminescence at surface |
| Radio immunoassay (RIA) | Radio isotope | None | Radiation at surface |
| Colloidal gold assay | Colloidal gold | (optional) plating solution to increase size of colloids | Colourimetry at surface |

5.0 Applications for Use of the Measurement System

The biological measurement system 10 can be used in applications where the sample is not sputum and/or mucus. Possible other samples for analysis by the system 10 include, for example, one or more of:
- (a) blood;
- (b) urine;
- (c) pathogenic sera;
- (d) semen;
- (e) saliva;
- (f) tears; and
- (g) sweat.

Moreover, the measurement system 10 can also be adapted to interrogate airborne particles such as airborne micro-organisms, spores, pollen, or airborne dust (for example from chemical processing plants where dangerous chemicals are used and/or manufactured).

The measurement system 10 described in the foregoing can be adapted for use in the detection of many other bacterial and viral infections including, but not limited to:
- (a) other forms of pneumonia such as influenzal pneumonia or viral pneumonia;
- (b) tuberculosis;
- (c) malaria;
- (d) diptheria;
- (e) lupuserethemytosis;
- (f) pertussis;
- (g) other zymotic diseases;
- (h) *streptococcus*; and *staphylococcus*.

The measurement system 10 can also be applied to detect viral particles, allergens or spores, pollen or other particles of a biological nature, or particles which are non-organic but can be detected by antibodies, nucleic acids or other suitable recognition groups. Such non-organic particles can include airborne particles of toxic compounds, controlled narcotics, explosives or any other particles that are present in air, water and other liquids.

Moreover, the measurement system 10 can be adapted to detect sympathetic particles such as indicators of certain forms of cancer.

Moreover, the measurement system 10 can be applied to detect particles that do not cause disease, such as antibodies. Thus, the measurement system 10 can be readily adapted for use in the early detection of HIV and AIDS, thereby being potentially valuable technology for countries such as South Africa, which is having to cope with such diseases.

It will be appreciated that the aforementioned biological measurement system 10 can be modified. For example, although antibodies are used to recognise and bind particles to be interrogated for pathogens, other recognition groups can be employed. For example, one or more of the following substances can be used:
- (a) proteins such as enzymes;
- (b) aptamers of other sequences of nucleic acid or nucleic acid analogues;
- (c) analogues of proteins;
- (d) artificial polypeptides; and
- (e) entire organisms.

If the particles in the sample are themselves fluorescent, they can be interrogated directly to generate the radiation; such particles circumvent the need for treatment with fluorescently-labeled antibodies as described in the foregoing.

Figure 16:
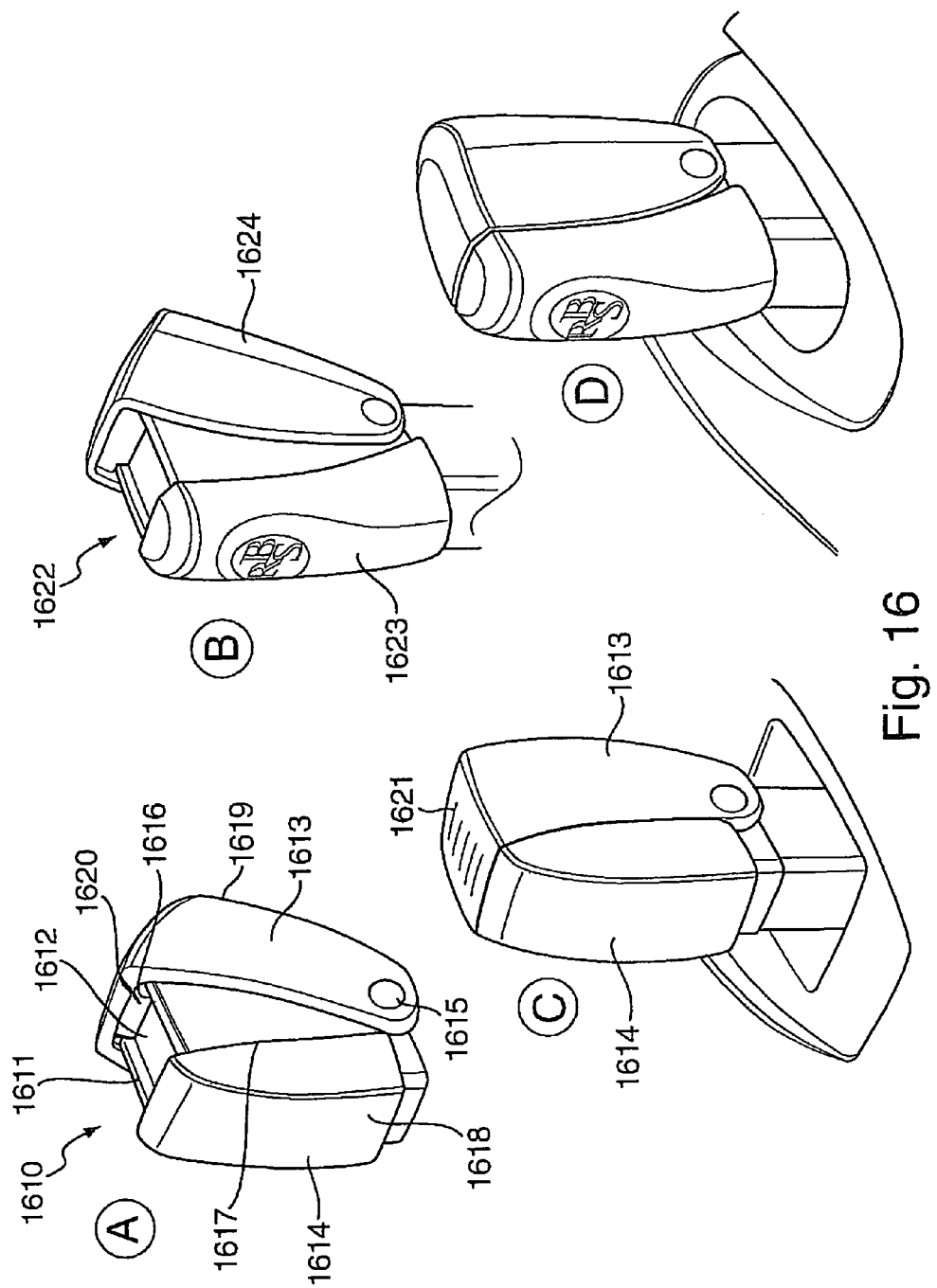
FIG. 16a shows a sample collection apparatus in a first perspective view where the sample collection apparatus is in its open position.
FIG. 16c shows the sample collection apparatus of FIG. 16a in its closed position and in engagement with an interrogation apparatus.
FIG. 16b shows a further sample collection apparatus in its open position whilst
FIG. 16d shows the sample collection apparatus of FIG. 16b in its closed position.

FIG. 16*a* shows a sample collection apparatus 1610 with a vessel 1611 comprising an upper recessed portion 1612 onto which a liquid sample may be deposited. The liquid sample may be of the kind discussed above. The bottom wall of the recessed portion 1612 incorporates an interrogation region which may be the other surface of a prism of the kind described above.

The vessel incorporates two mating halves 1613 and 1614 which open up as a jaw in order to reveal the recess portion in a first mode of use and form an enclosure in a second mode of use when the jaws a brought together in a closed position. Half 1613 forms a lid which is hinged to half 1614 which forms a body. A hinge 1615 is provided at the lower extremity of the sample collection apparatus. Lid 1613 incorporates an inner bowed surface 1616 which corresponds to an inner bowed surface 1617 of body 1614. Apparatus 1610 also incorporates bowed outer surfaces 1618 and 1619. On the other side of the upper wall of lid 1613, a wiper blade 1620 is provided and is of sufficient length to engage the interrogation surface in order to automatically spread the sample over the prism as the lid is closed. A catch may be provided to lock the lid in place once shut to create a tamperproof and a safely disposable unit.

As shown in FIG. 16*c*, half 1613 and 1614 lock together in a fully enclosing position. The upper surface 1621 incorporates a number of ribs or knurls to offer an increased in friction to facilitate the application of a user's thumb to cause the apparatus to change from its open position as shown in FIG. 16*a* to its closed position as shown in FIG. 16*c*. The lower portion of the apparatus incorporates an aperture which mates with a correspondingly shaped interrogation apparatus, which may be of the kind illustrated above with reference to FIG. 1 for example.

FIG. 16b shows a similar sample collection apparatus 1622 to the embodiment of 16a. The main difference between the two embodiments concerns the directions of the bowed surfaces. Surfaces 1623 and 1624 are cylindrical relative to the longitudinal axis of the sample collection apparatus. In FIG. 16d, the interrogation apparatus to which the sample collection apparatus is fitted appears to have correspondingly bowed receiving portions.

Figure 17:
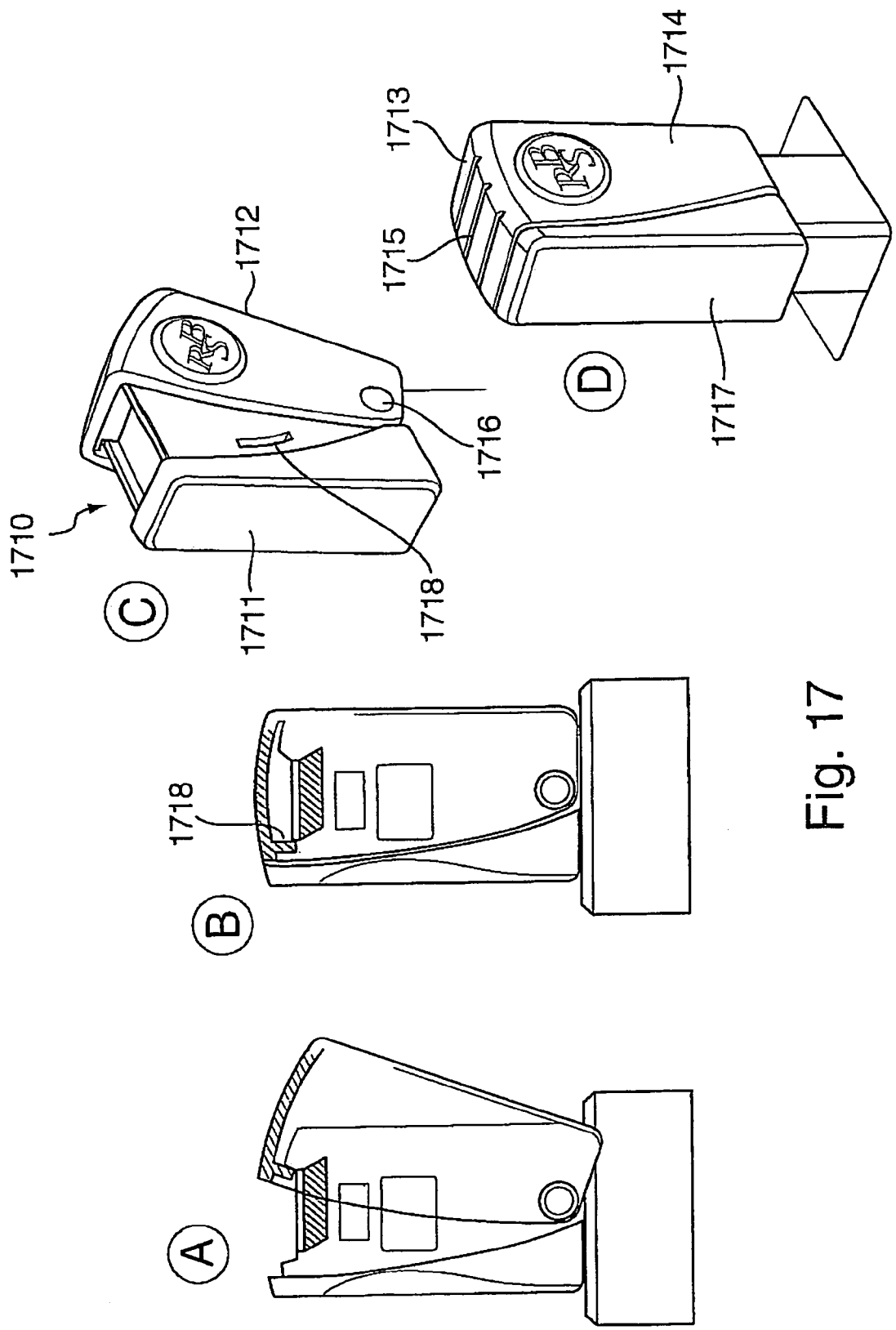
FIG. 17a shows a further embodiment of a sample collection apparatus in its opened position whilst
FIG. 17b shows the sample collection apparatus of FIG. 17a in its closed position.
FIG. 17c shows the embodiment of FIG. 17a in its open position from a perspective view whilst
FIG. 17d shows the sample collection apparatus of FIG. 17a in its closed position and in a perspective view.

The embodiment of FIG. 17 is similar to embodiments of FIGS. 16a and 16b. Instead of the bowed side faces, the apparatus 1710 presents a flat side face 1711 and a flat side face 1712. The upper surface 1713 of the lid 1714 incorporates a number of troughs 1715 or ribs in order to form an area of high friction to facilitate the closure of the apparatus. Hinge 1716 is also envisaged to allow the rotation of the lid 1714 relative to body 1717. As shown in FIG. 17d the hinge may be located as an integral part of the lid in order to be invisible from the outside of the apparatus. The hinge may be formed, for example, by a shaft portion projecting inwardly from the wall of lid 1714.

FIG. 17c shows a catch 1718 which may be formed as a projecting rib or as a recessed portion to allow the lid to snap-fit onto the body 1717 when the lid is closed.

In FIG. 17b, wiper blade 1718 is shown with a certain degree of clearance relative to the prism. Alternatively, the wiper blade may directly engage the prism dependant upon the spreading effect desired for a particular sample type.

Figure 18:
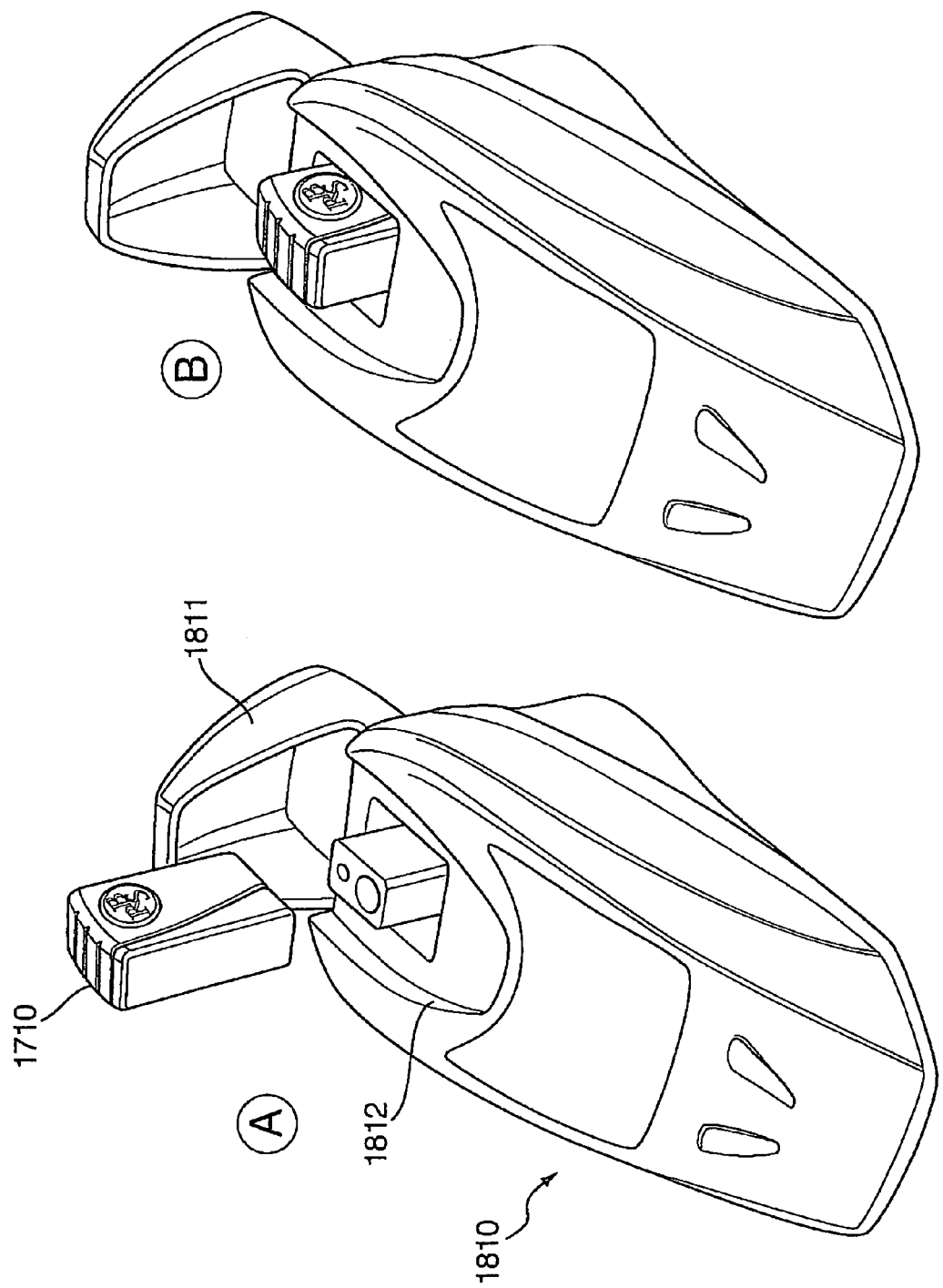

Sample collection apparatus 1710 is shown in its closed position in FIG. 18a prior to engagement with interrogation apparatus 1810. The interrogation apparatus may itself also include a hinged lid 1811 which fits in a corresponding recessed portion 1812.

FIG. 18b shows sample collection apparatus 1710 in its fully engaged position for interrogation purposes.

Figure 19:
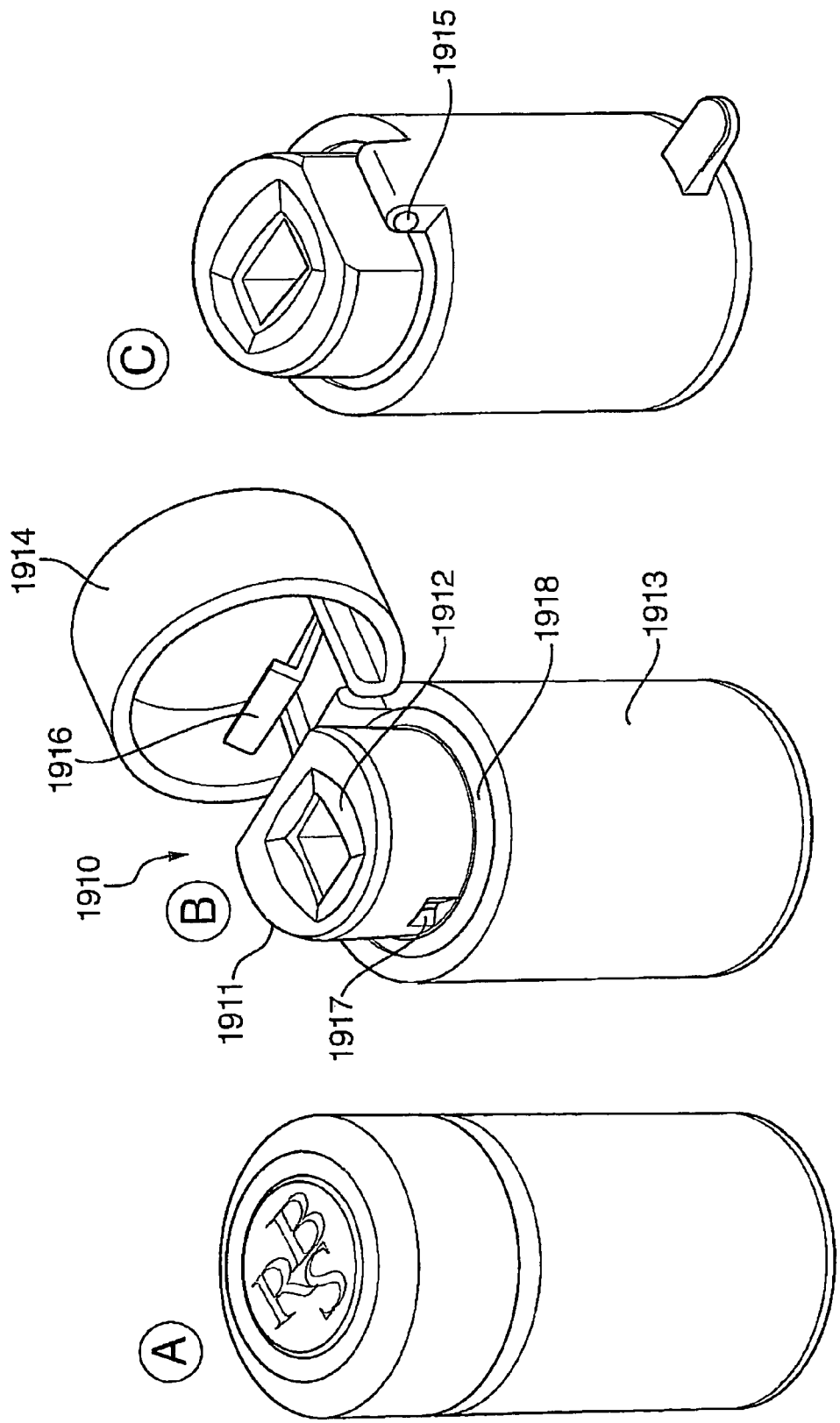
FIG. 19a shows a perspective view of a further embodiment of a sample collection apparatus with its lid in a shut position.
FIG. 19b shows a perspective view of the sample collection apparatus in its open configuration.
FIG. 19c shows a sample collection apparatus as shown in FIGS. 19a and 19b with its lid removed.

The embodiment of FIG. 19 shows a sample collection apparatus 1910, which similarly incorporates a vessel 1911 with a recessed portion 1912 for collecting a sample for interrogation purposes. Vessel 1911 is formed of a body 1913 and a lid 1914 which when closed against body 1913 fully encloses a sample. Lid 1914 is hinged as shown in FIGS. 19b and 19c. Hinge 1915 is shown in FIG. 19c. The lower wall of recessed portion 1912 incorporates an interrogation region in the form of the top surface of a prism. A wiper blade 1916 extends from the upper surface of lid 1914 in order to engage the interrogation region as the lid is shut onto body 1913. As the lid is shut, the wiper blade spreads the sample in order to prepare it for interrogation. A catch 1917 is provided in order to lock the sample collection apparatus in its closed position. This provides an apparatus which is both tamperproof and ideally suited for disposal.

The apparatus of FIG. 19 has an overall cylindrical shape, which is circular in cross section. The lid configuration allows the sealing area to be relatively small and localised at the top of the apparatus. The wiper blades illustrated in the previous embodiments may be flexible in nature. They may also be heat welded, co-molded, or even formed through double injection. A gasket feature, such as gasket feature 1918, is also envisaged to seal the lid to the body. This feature may be co-molded if required.

In at least one of the previous embodiments if not in each of the previous embodiments, results are obtained in a timescale of minutes or possibly under 5 minutes.

The invention claimed is:

1. A sample collection apparatus comprising:
    a collection vessel comprising a lid having an inside face and a body having a recessed portion for receipt of a sample, which recessed portion defines an optical interrogation region in said body;
    a hinge connecting said lid and said body, said lid being able to pivot about said hinge from an open position to a closed position relative to said body, wherein in said open position, said recessed portion is exposed to receive a sample and in said closed position, said lid engages said body and encloses said recessed portion to enclose the sample; and
    a spreader which is located on said inside face of said lid and which is elastically deformable, said spreader being positioned to spread the sample over said optical interrogation region as said lid is pivoted from said open position to said closed position.

2. An apparatus according to claim 1, further comprising marking means for optically labelling components present in the sample to produce labelled components.

3. An apparatus according to claim 2, wherein said marking means comprises fluorescent markers comprising an intermediate carrier comprising latex spheres, antibodies, and fluorophores bound to said antibodies by way of said intermediate carrier, such that a plurality of said fluorophores are associated with each of said antibodies, whereby said marking means are for optically marking the presence of said components present in the sample by an assay.

4. An apparatus according to claim 1, wherein said collection vessel is arranged to enclose the sample, thereby preventing personnel contact with the sample when said apparatus is in use.

5. An apparatus according to claim 1, wherein said collection vessel is of the single-use disposable type.

6. An apparatus according to claim 2, wherein said marking means comprises lysing means for causing lysis of said components present in the sample, thereby enhancing measurement sensitivity of said apparatus by increasing the number of available potential optical labelling sites.

7. An apparatus according to claim 1, wherein said recessed portion has a wall defining said optical interrogation region.

8. An apparatus according to claim 1, wherein in said closed position said lid engages said body in a non-releasable manner.

9. An apparatus according to claim 8, wherein said lid and said body include means for snap-fit engagement for securing said lid against said body when in said closed position.

10. A method of detecting at least one pathogen in at least one sample from a subject comprising the steps of:
    (a) providing a sample collection apparatus comprising a collection vessel comprising a lid having an inside face and a body having a recessed portion for receipt of a sample, which recessed portion defines an optical interrogation region in said body; a hinge connecting said lid and said body, said lid being able to pivot about said hinge from an open position to a closed position relative to said body, wherein in said open position, said recessed portion is exposed to receive a sample and in said closed position, said lid engages said body and encloses said recessed portion to enclose the sample; and a spreader which is located on said inside face of said lid and which is elastically deformable, said spreader being positioned to spread the sample over said optical interrogation region as said lid is pivoted from said open position to said closed position;

(b) collecting said sample in the collector;
(c) spreading said sample over said interrogation region;
(d) optically labeling a pathogen present in said sample;
(e) optically interrogating the pathogens to achieve an optical response; and
(f) determining from the optical response of said sample whether or not a pathogen is present in said sample.

* * * * *